United States Patent
Hayashi et al.

(10) Patent No.: US 10,138,527 B2
(45) Date of Patent: Nov. 27, 2018

(54) METHOD FOR MONITORING DIFFERENTIATION INTO CARDIAC MUSCLE CELLS

(71) Applicant: OLYMPUS CORPORATION, Tokyo (JP)

(72) Inventors: Taro Hayashi, Tachikawa (JP); Isao Sakane, Hachioji (JP); Yoko Ohashi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/298,723

(22) Filed: Oct. 20, 2016

(65) Prior Publication Data

US 2017/0037483 A1 Feb. 9, 2017

Related U.S. Application Data

(63) Continuation of application No. PCT/JP2014/076193, filed on Sep. 30, 2014.

(30) Foreign Application Priority Data

Apr. 22, 2014 (JP) ................. 2014-088601

(51) Int. Cl.
| | |
|---|---|
| *C12Q 1/6897* | (2018.01) |
| *C12N 5/077* | (2010.01) |
| *G01N 21/64* | (2006.01) |
| *G01N 33/483* | (2006.01) |
| *G06K 9/00* | (2006.01) |
| *G06T 7/00* | (2017.01) |
| *G06T 7/20* | (2017.01) |

(52) U.S. Cl.
CPC ......... *C12Q 1/6897* (2013.01); *C12N 5/0657* (2013.01); *G01N 21/6486* (2013.01); *G01N 33/4833* (2013.01); *G06K 9/00134* (2013.01); *G06T 7/0012* (2013.01); *G06T 7/0022* (2013.01); *G06T 7/20* (2013.01); *G06T 7/97* (2017.01); *C12N 2506/02* (2013.01); *C12N 2506/45* (2013.01); *C12N 2510/00* (2013.01); *G06T 2207/10056* (2013.01); *G06T 2207/10064* (2013.01); *G06T 2207/30048* (2013.01)

(58) Field of Classification Search
CPC .................................................. C12Q 1/6897
See application file for complete search history.

(56) References Cited

FOREIGN PATENT DOCUMENTS

| | | |
|---|---|---|
| JP | 2012-095627 A | 5/2012 |
| JP | 2012-194168 A | 10/2012 |
| JP | 2013-53854 A | 3/2013 |
| JP | 2013-192468 A | 9/2013 |
| JP | 2013-195127 A | 9/2013 |
| JP | 2014-33617 A | 2/2014 |
| WO | WO 2007/080622 A2 | 7/2007 |
| WO | WO 2010/101225 A1 | 9/2010 |
| WO | WO 2011/029798 A1 | 3/2011 |
| WO | WO 2011/118655 A1 | 9/2011 |
| WO | WO 2013/137491 A1 | 9/2013 |

OTHER PUBLICATIONS

English translation of International Preliminary Report on Patentability dated Nov. 3, 2016 together with the Written Opinion received in related International Application No. PCT/JP2014/076193.
International Search Report dated Nov. 4, 2014 issued in PCT/JP2014/076193.
Taro Hayashi et al., "Hakko Imaging ni yoru Shinkin Bunka Marker I dens hi Hatsugen no Kashika", Regenerative Medicine, Jan. 27, 2014 (Jan. 27, 2014), vol. 13, special extra issue, p. 323, P-2-064.
B. Hebert et al., "Spatiotemporal image correlation spectroscopy (STICS) theory, verification, and application to protein velocity mapping in living CHO cells", Biophysical Journal (May 2005) vol. 88, pp. 3601-3614.
Jin et al., "Biochemical and Biophysical Research Communications", Sep. 25, 1995 vol. 214, No. 3, pp. 1168-1174.
Japanese Office Action dated Dec. 5, 2017 in Japanese Patent Application No. 2014-088601.
Japanese Decision of Rejection dated Jul. 31, 2018 received in Japanese Patent Application No. 2014-088601, together with an English-language translation.

*Primary Examiner* — Catherine S Hibbert
(74) *Attorney, Agent, or Firm* — Scully, Scott, Murphy & Presser, P.C.

(57) ABSTRACT

A method for monitoring differentiation into cardiac muscle cells includes keeping, in an alive state, cells into which a reporter gene of luminescent protein configured to vary in luminescence intensity according to an expression of myocardial differentiation marker gene is introduced. The method includes acquiring a luminescence image as a still image by imaging light emitted from the cells in a light shielding state. The method includes acquiring sequential images with illuminating the cells. The method includes associating biological information obtained from the sequential images with biological information obtained from the still image.

9 Claims, 36 Drawing Sheets

Specification includes a Sequence Listing.

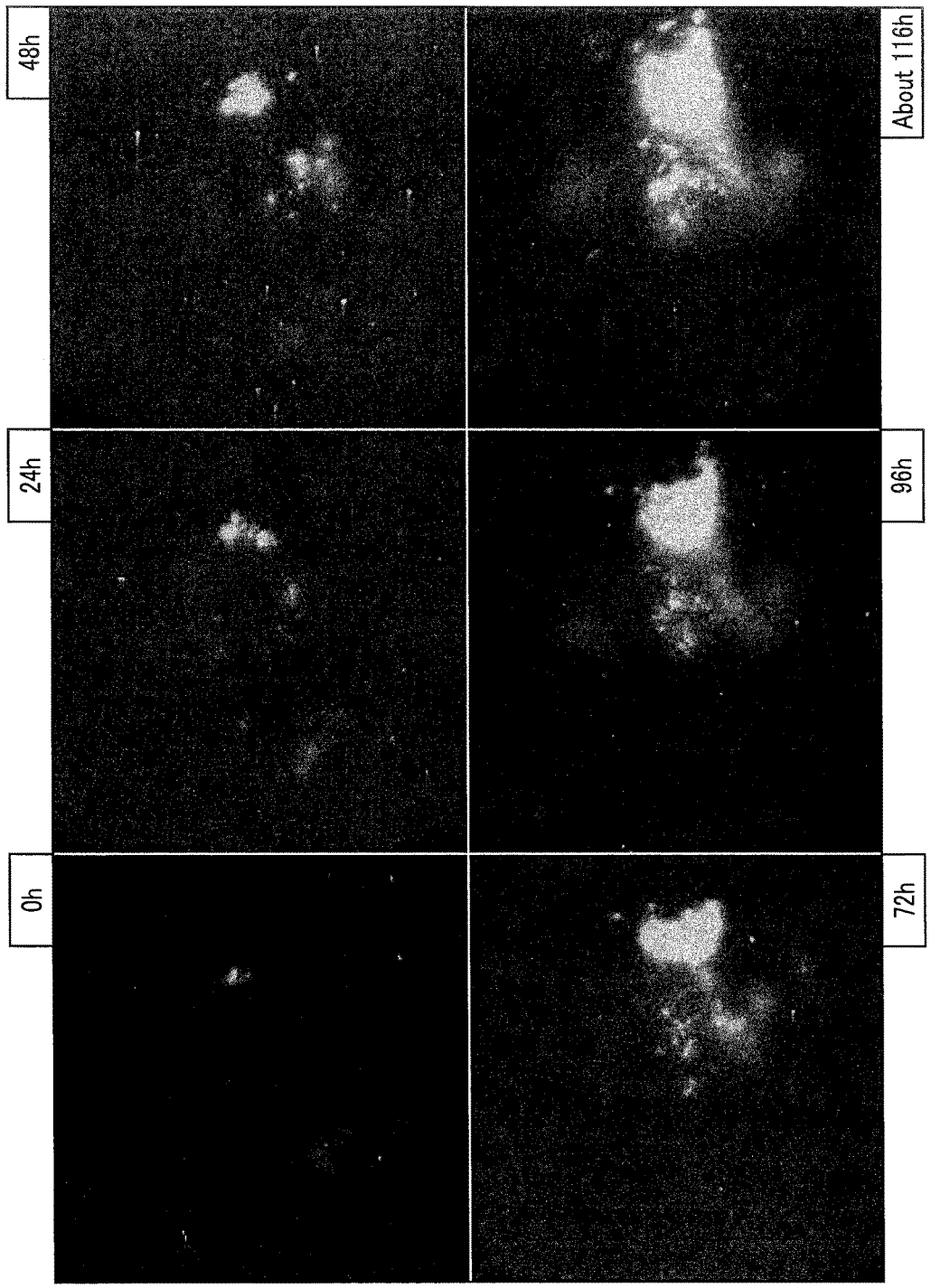
F I G. 10

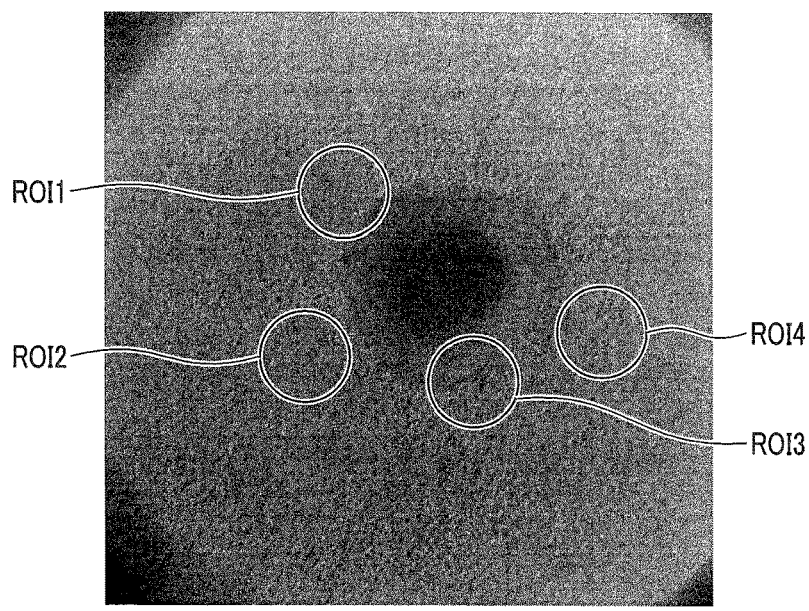
F I G. 11
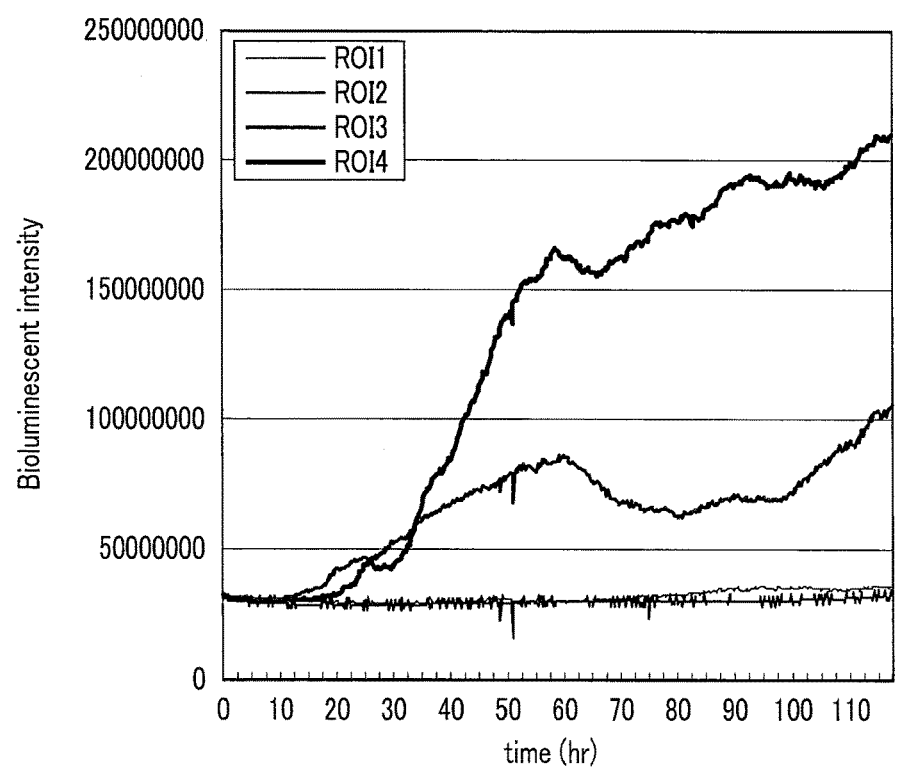
F I G. 12

| Time after start of observation | Bright-field | STICS/gene expression | Beating |
|---|---|---|---|
| 66 hours | | | |
| 71 hours | | | |
| 76 hours | | | |
| 81 hours | | | |
| 86 hours | | | |
| 91 hours | | | |

F I G. 15

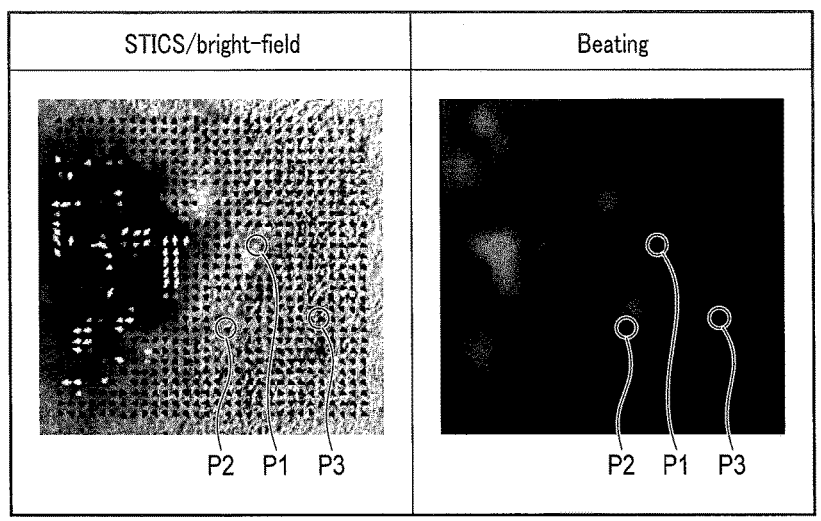
F I G. 16A

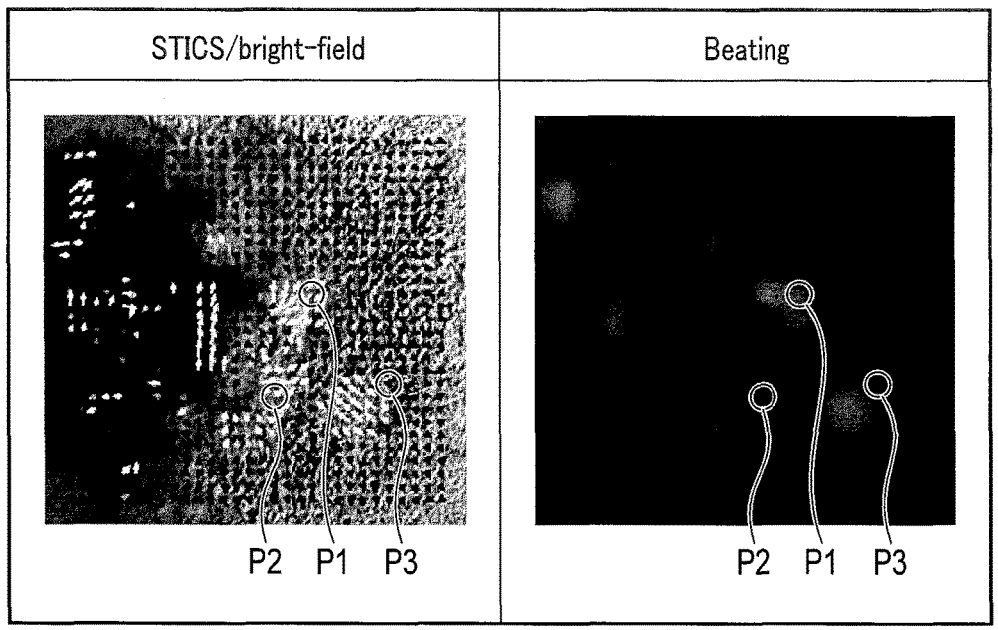
F I G. 17A

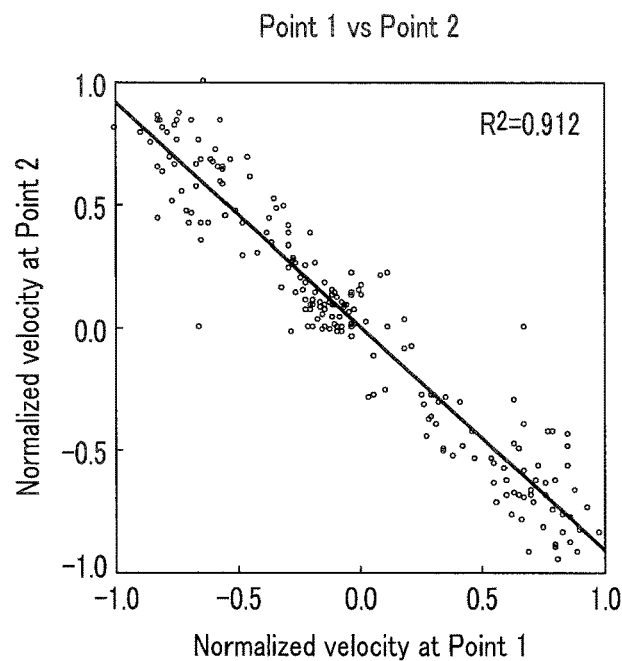
F I G. 17C
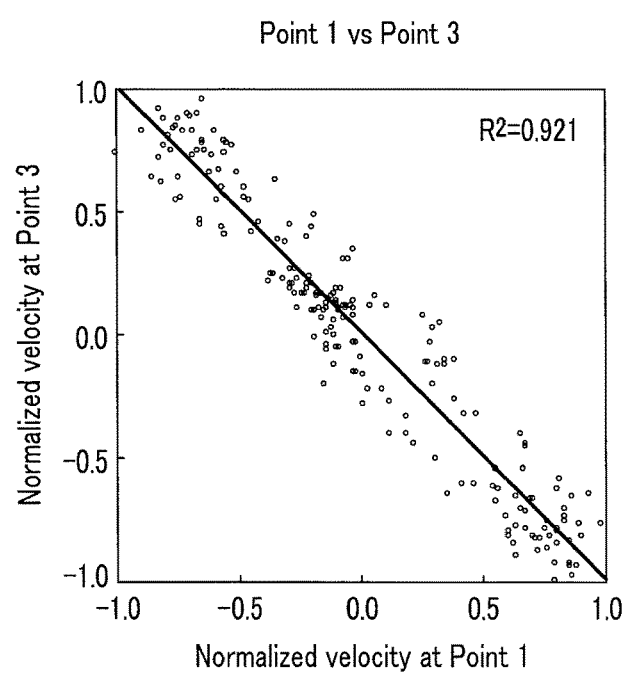
F I G. 17D

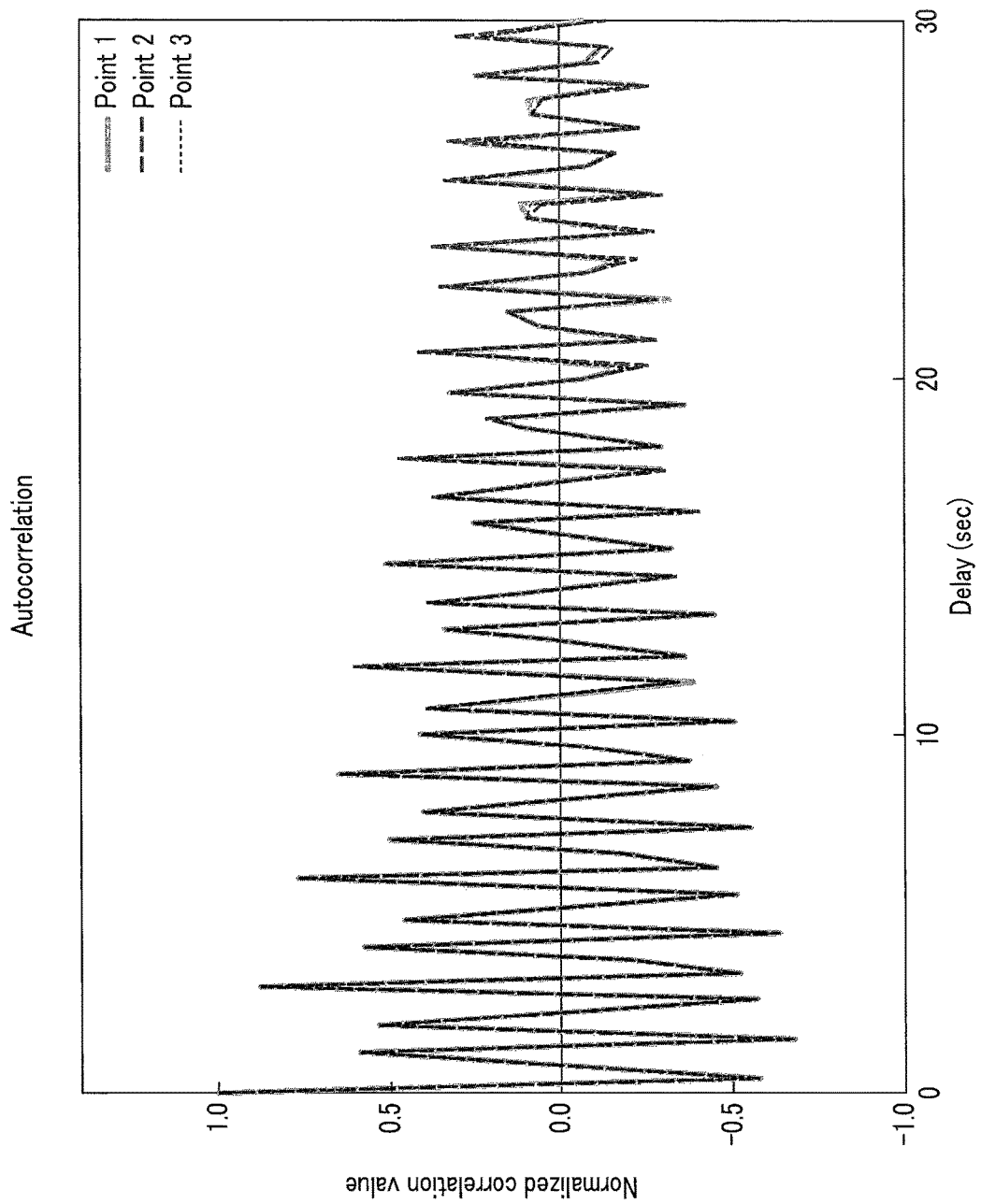
F I G. 17F

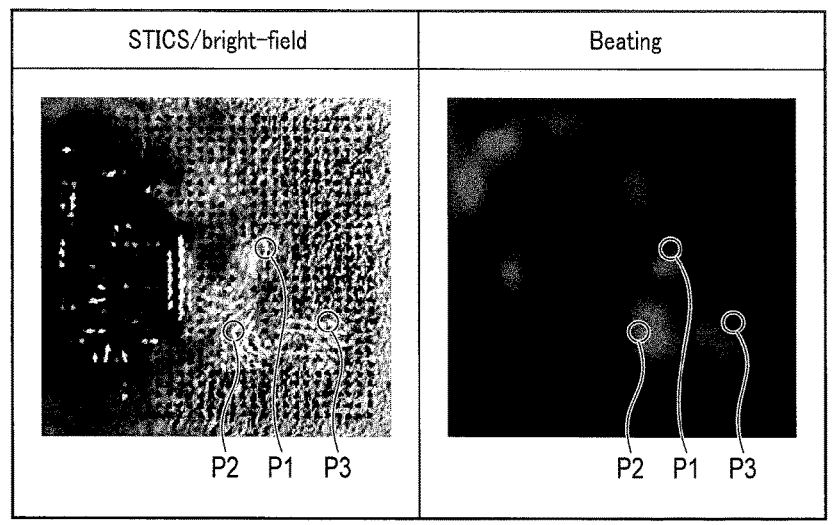
F I G. 18A

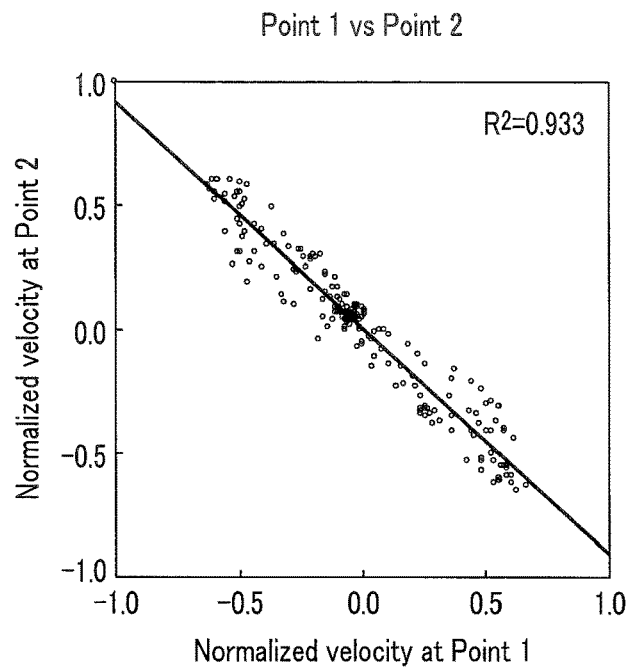
F I G. 18C
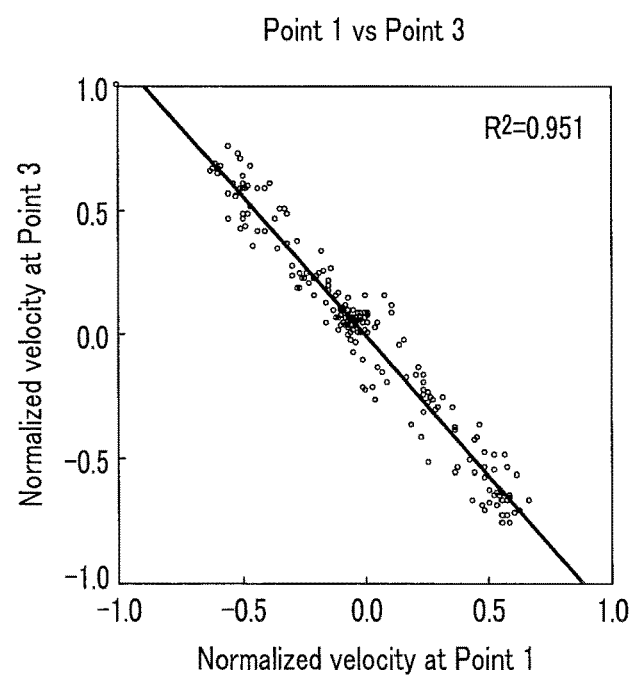
F I G. 18D

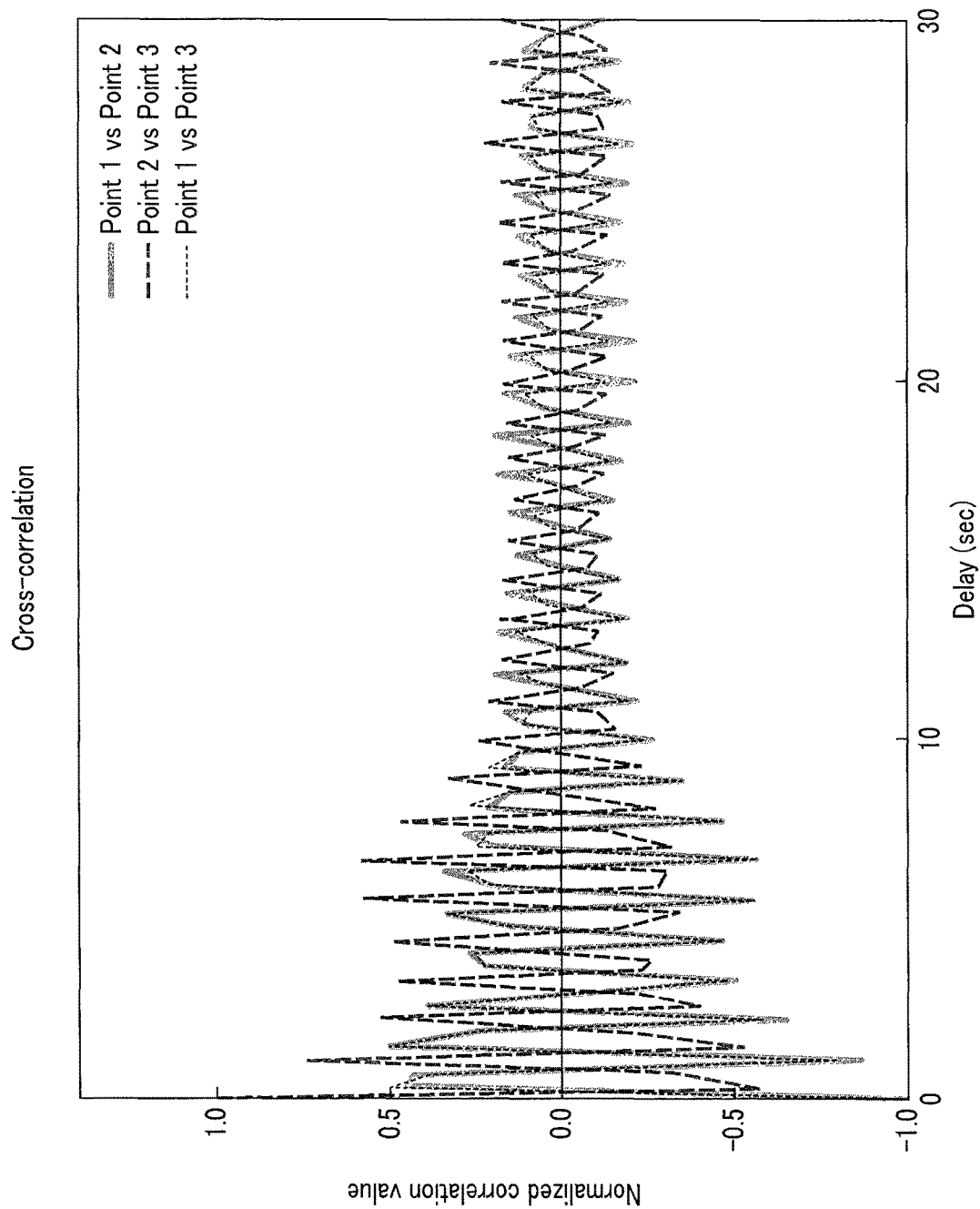
F I G. 18G

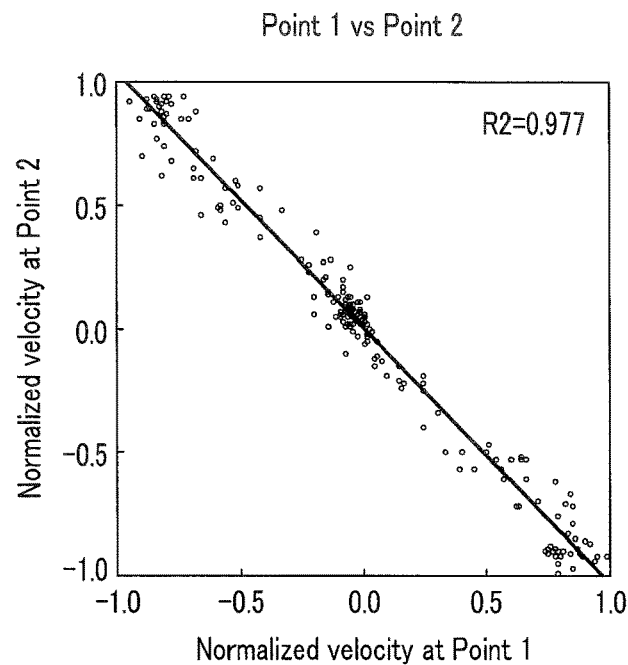
F I G. 19C
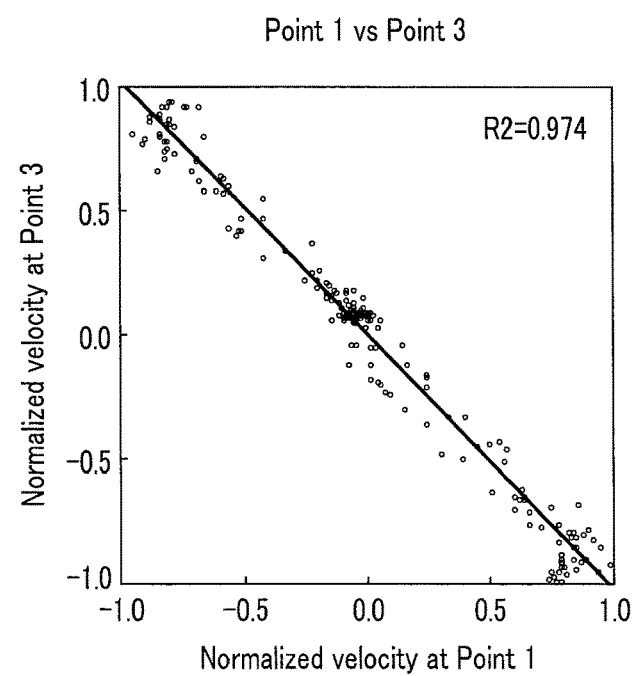
F I G. 19D

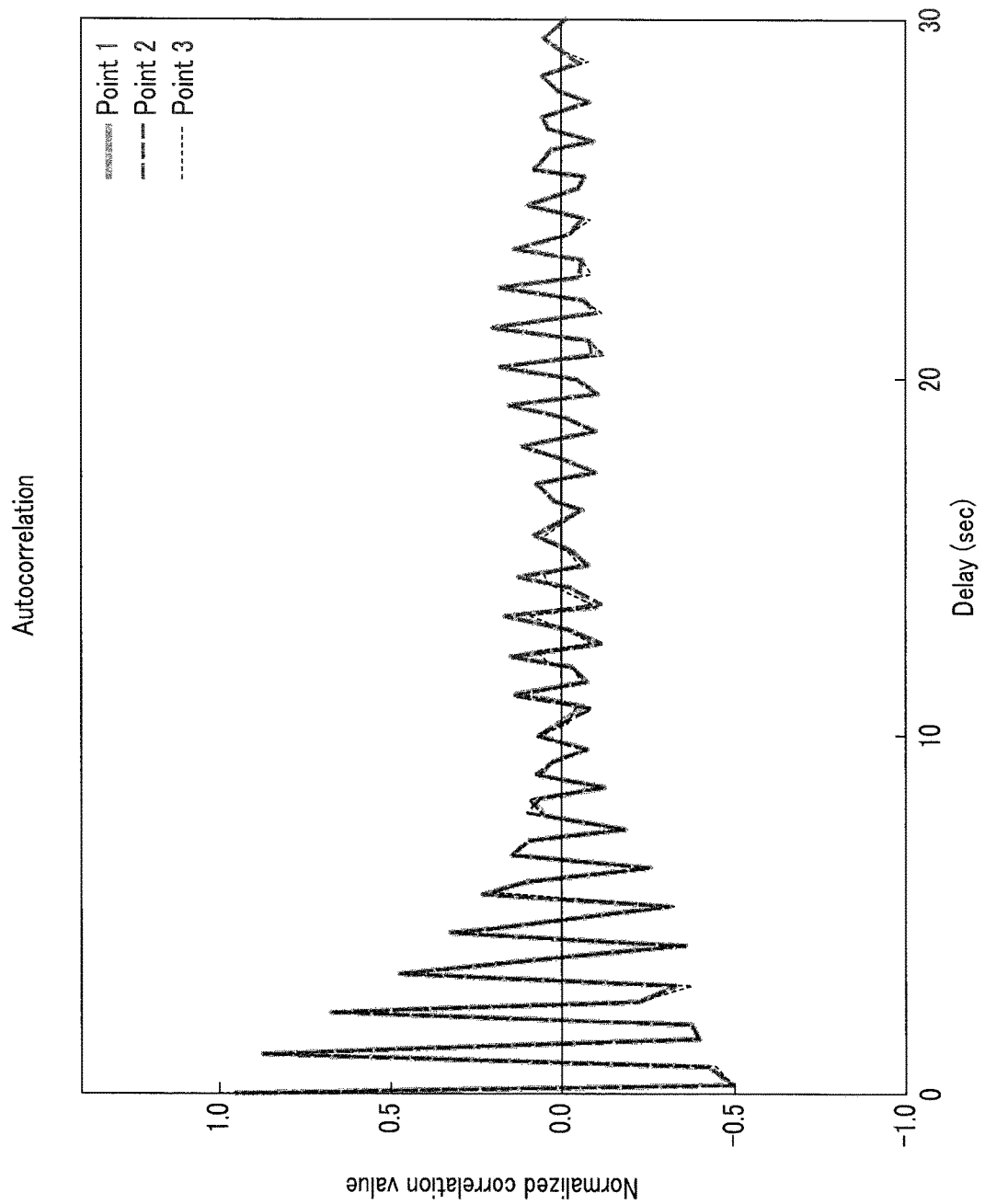
F I G. 19F

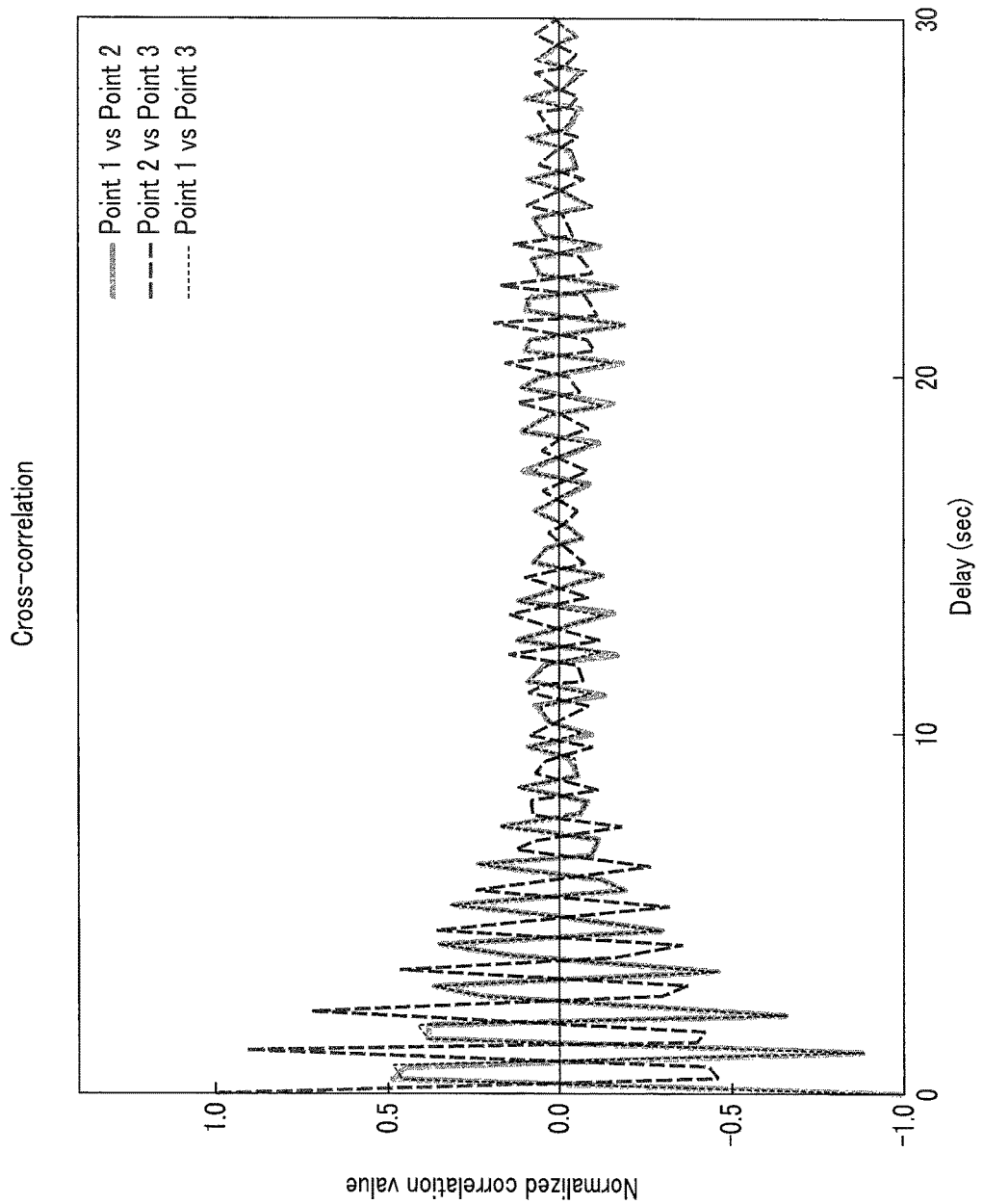
F I G. 19G

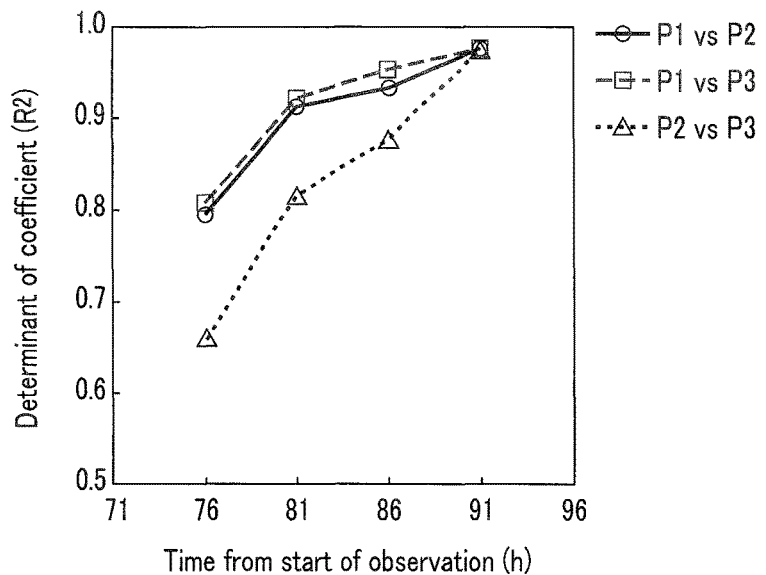
F I G. 20
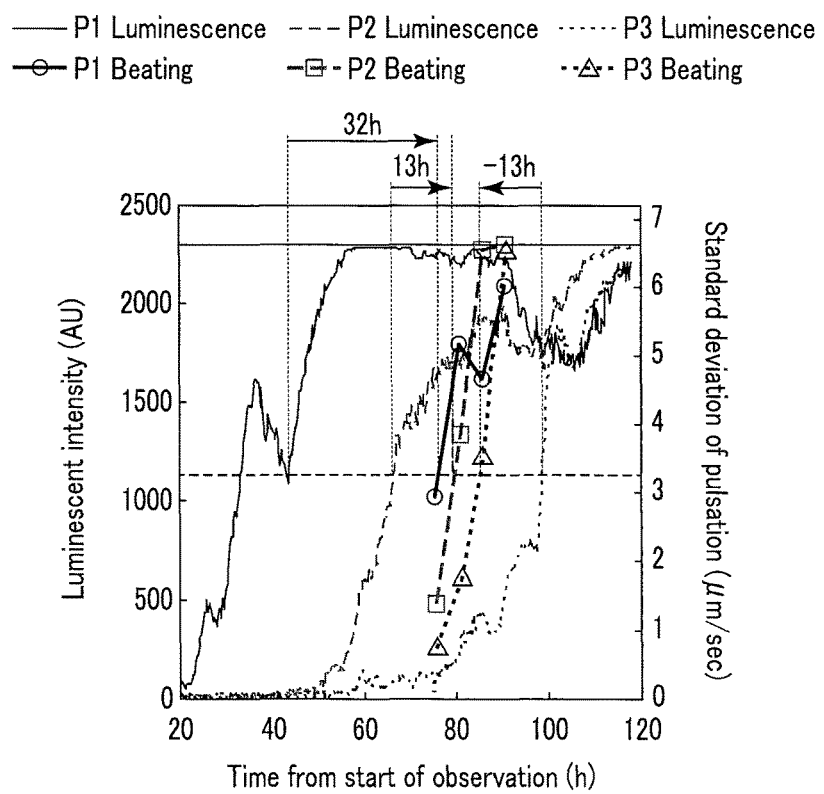
F I G. 21

METHOD FOR MONITORING DIFFERENTIATION INTO CARDIAC MUSCLE CELLS

CROSS-REFERENCE TO RELATED APPLICATIONS

This application is a Continuation Application of PCT Application No. PCT/JP2014/076193, filed Sep. 30, 2014 and based upon and claiming the benefit of priority from prior Japanese Patent Application No. 2014-088601, filed Apr. 22, 2014, the entire contents of all of which are incorporated herein by reference.

INCORPORATION BY REFERENCE OF SEQUENCE LISTING

The Sequence Listing in an ASCII text file, named as 34215Z_Sequence_Listing.txt of 1 KB, created on Oct. 20, 2016, and submitted to the United States Patent and Trademark Office via EFS-Web, is incorporated herein by reference.

BACKGROUND OF THE INVENTION

1. Field of the Invention

The present invention relates to a method for monitoring differentiation into cardiac muscle cells.

2. Description of the Related Art

At present, regenerative medicine to regenerate affected parts or parts lost by diseases is drawing attention in the medical field. In the field of such regenerative medicine, attention is drawn to attempts to differentiate, into cardiac muscle cells, stem cells such as embryonic stem cells (ES cells) or induced pluripotent stem cells (iPS cells) having differentiation potency into various cells, and to use the cardiac muscle cells in the treatment of patients having diseases such as myocardial infarction.

However, many points are still unknown regarding the mechanism in which ES cells and iPS cells differentiate into various cells. Investigating how genes are expressed in the process of differentiation is extremely important in clarifying differentiation processes.

One method of analyzing gene expression is a technique of transcriptional activity measurement using reporter genes. The technique of transcriptional activity measurement includes an analysis of a gene expression control sequence such as a promoter, an enhancer, and a silencer, and transcription factors bound thereto. This technique also includes using the expression level of the reporter genes connected to a certain promoter as an index to analyze various intracellular molecular mechanisms, for example, to analyze the activation state of intracellular signaling pathways or analyze receptors and ligands. This technique is also used as a tool for large scale screening in drug discovery and as an index of toxicity assessment of chemical substances.

In general, techniques such as fluorescence imaging using fluorescent protein such as GFP, antibody staining, western blotting, flow cytometry and so on are used in the analysis of gene expression in a differentiation-inducing process of stem cells such as ES cells and iPS cells.

However, the problem of the fluorescence imaging is that quantitatively observing gene expression with time for a long period is difficult because of optical damage caused by excitation light, influence of autofluorescence, and a case where a desired amount of light may not reach due to the scattering of excitation light inside an embryoid body comprising cell groups that have differentiated. The problem of the antibody staining and the western blotting is that gene expression of the same target cannot be observed with time because a sample needs to be fixed.

Recently, not only fluorescence imaging using fluorescent protein but also luminescence imaging using bioluminescence of luminescent living organisms typified by fireflies has been performed. The bioluminescence is a phenomenon in which visible light is emitted by living organisms or substances derived therefrom due to various chemiluminescence reactions without dependence on optical energy resulting from illumination light. The bioluminescence reactions mostly require three components: luciferin (substrate), luciferase (enzyme), and molecular enzyme.

Luciferase is used as reporter genes for assessment of influence of exogenous factors on cells, intracellular information transmission, expression analyses of individual protein groups and so on. In a system in which luciferase is used, for example, firefly luciferase genes are first inserted into a transcriptionally activated site. A genetic construct is then introduced into cells. Cultured cells into which the reporter genes have been introduced are then treated with, for example, a drug for a predetermined time. The cells are then collected, and a luminescent substrate is added thereto. As a result, the amount of luciferase synthesized in the cells is measured, and transcriptional activity can be assessed.

Luminometers are generally used to assess the transcriptional activity of reporter assays using luciferase. However, the luminometers are intended to measure luminescence of all cells present in a well. Cells need to be dissolved depending on protocols. Therefore, the change of the luminescent intensity of each cell cannot be measured with time in the same cell in the assays using the luminometers.

In the utilization in the regenerative medicine of stem cells such as ES cells and iPS cells, it is reported that the degree and characteristics of gene expression vary from strain to strain. The challenge is therefore to adjust and maintain cells of uniform quality. It is thus necessary to clarify, on an individual single cell level, how genes are expressed in the differentiation-inducing process of ES cells and iPS cells.

Techniques to image stem cells such as ES cells and iPS cells are disclosed in International Publication No. 2011/029798 and International Publication No. 2007/080622. However, the techniques disclosed in International Publication No. 2011/029798 and International Publication No. 2007/080622 are techniques to measure the total of gene expression of stem cells by the luminometer or methods to transplant stem cells into a mouse body and then image the stem cells in the living body. That is, the techniques disclosed in International Publication No. 2011/029798 and International Publication No. 2007/080622 are not intended to image gene expression on an individual cell level.

A technique to monitor the differentiation of stem cells such as ES cells and iPS cells and the expression of genes involved in differentiation is disclosed in International Publication No. 2010/101225. The antibody staining method is used in the technique disclosed in International Publication No. 2010/101225. In this case, cells need to be fixed, and endpoint data alone are obtained. Moreover, fluorescence is used as a means of detection in the antibody staining. Cells having integrated structures such as a cell sheet or an embryoid body have strong autofluorescence. Therefore, a quantitative analysis using fluorescence is difficult in some cases.

BRIEF SUMMARY OF THE INVENTION

According to an aspect of the invention, a method for monitoring differentiation into cardiac muscle cells includes keeping, in an alive state, cells into which a reporter gene of luminescent protein configured to vary in luminescence intensity according to an expression of myocardial differentiation marker gene is introduced; acquiring a luminescence image as a still image by imaging light emitted from the cells in a light shielding state; acquiring sequential images by illuminating the cells; and associating biological information obtained from the sequential images with biological information obtained from the still image.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 10 is a luminescence image in which expression of cTnT in the process of myocardial differentiation of the embryoid body derived from the mouse iPS cells is observed with time;

FIG. 11 is a diagram showing ROI1 to ROI4;

FIG. 12 is a diagram showing the change of the luminescent intensity of the luminescence image shown in FIG. 10, in which expression of cTnT in the process of myocardial differentiation of the embryoid body derived from the mouse iPS cells is observed with time, and shows results of analyses regarding ROI1 to ROI4 shown in FIG. 11;

FIG. 15 is a diagram showing bright-field sequential images, images in which analytic results obtained by the image correlation method are superimposed on luminescence images, and images showing beating intensities, the images being obtained after 66 hours, 71 hours, 76 hours, 81 hours, 86 hours, and 91 hours from the start of observation;

FIG. 16A is a diagram showing an image in which an analytic result obtained by the image correlation method is superimposed on a bright-field image of cells, and an image showing beating strength after 76 hours from the start of observation;

FIG. 17A is a diagram showing an image in which an analytic result obtained by the image correlation method is superimposed on a bright-field image of cells, and an image showing beating strength after 81 hours from the start of observation;

FIG. 17C is a diagram showing how the velocity relation between the first point P1 and the second point P2 is after 81 hours from the start of observation;

FIG. 17D is a diagram showing how the velocity relation between the first point P1 and the third point P3 is after 81 hours from the start of observation;

FIG. 17F is a diagram showing how an autocorrelation of velocity is after 81 hours from the start of observation;

FIG. 18A is a diagram showing an image in which an analytic result obtained by the image correlation method is superimposed on a bright-field image of cells, and an image showing beating strength after 86 hours from the start of observation;

FIG. 18C is a diagram showing how the velocity relation between the first point P1 and the second point P2 is after 86 hours from the start of observation;

FIG. 18D is a diagram showing how the velocity relation between the first point P1 and the third point P3 is after 86 hours from the start of observation;

FIG. 18G is a diagram showing how a cross-correlation of velocity is after 86 hours from the start of observation;

FIG. 19C is a diagram showing how the velocity relation between the first point P1 and the second point P2 is after 91 hours from the start of observation;

FIG. 19D is a diagram showing how the velocity relation between the first point P1 and the third point P3 is after 91 hours from the start of observation;

FIG. 19F is a diagram showing how an autocorrelation of velocity is after 91 hours from the start of observation;

FIG. 19G is a diagram showing how a cross-correlation of velocity is after 91 hours from the start of observation;

FIG. 20 is a diagram showing the relation between the elapsed time from the start of observation and the coefficient of determination; and FIG. 21 is a diagram showing the relation between the elapsed time from the start of observation and beating strength as well as luminescent intensity.

DETAILED DESCRIPTION OF THE INVENTION

Figure 1:
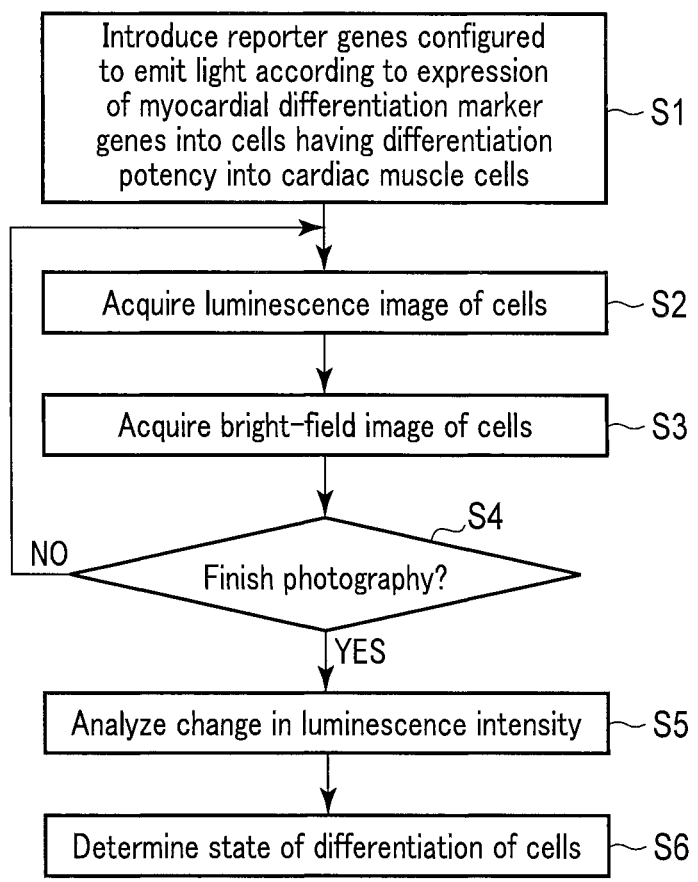
FIG. 1 is a flowchart showing an overview of a method of monitoring differentiation into cardiac muscle cells according to one embodiment.

One embodiment of the present invention is described. The present embodiment relates to a method of monitoring differentiation into cardiac muscle cells. An overview of the method according to the present embodiment is shown in FIG. 1.

As shown in step S1, the present method includes introducing reporter genes of luminescent protein configured to emit light according to the expression of myocardial differentiation marker genes into cells having differentiation potency into cardiac muscle cells. The myocardial differentiation marker means, for example, genes which are expressed in the process of the myocardial differentiation. The myocardial differentiation marker can include different genes.

The method according to the present embodiment includes marking at least one cell having the differentiation potency into the cardiac muscle cells with luminescent protein which emits light according to the expression of myocardial differentiation marker genes and/or undifferentiated marker genes. The method according to the present embodiment may also include using fluorescent protein such as green fluorescent protein (GFP) together. The method according to the present embodiment may additionally include the analysis of beating of cardiac muscle cells, calcium imaging to analyze the change of calcium ions in the cardiac muscle cells, and the measurement of an action potential of the cardiac muscle. Here, the beating refers to periodic motion of cell mass produced when cell masses bonded to each other cooperate to repeat contraction and relaxation. The beating phenomenon can be recognized when the position of the individual cell belonging to a cell mass periodically moves on a given orbit. It is microscopically observed that the individual cell typically reciprocates on a given straight line. The beating phenomenon can be clearly differentiated from positional displacement other than the beating by two points: the cells in the same cell mass moves in the same period; and individual cells move in a direction and magnitude similar to those of the cells therearound.

Recognizing the beating by taken images requires sequential images (movies) that are sequentially taken at a frame rate which is enough fast by comparison with the time required for the process of contraction and relaxation. The individual cell position in each frame can be determined manually or by various image recognition methods using images at previous frame and subsequent frame as clues. Beating can also be recognized by analyzing the motion of a light-dark pattern of an image in accordance with a method such as an optical flow or an image correlation method without specifying the individual cell positions. The calcium imaging includes introducing calcium-responsive luciferase such as obelin into cells, and imaging calcium response in the cells. The measurement of the action potential of the cardiac muscle is the measurement of the change of the potential of cells during beating in a state where an electrode for potential measurement is in contact with the cells.

The cells can be cells derived from various organisms. The cells can be, for example, cells derived from multicellular organisms. The cells can be, for example, cells derived from mammals such as a human or a mouse. The cells may be cultured cells. The cells may include a single kind of cells. The cells may include different kinds of cells.

The cells may have a layer structure such as a cell sheet. The cells have the differentiation potency. That is, the cells are undifferentiated cells, and are have the differentiation potency into at least the cardiac muscle. The cells can be, for example, progenitor cells which have differentiated to some degree but which can further differentiate into the cardiac muscle. The cells may advance differentiation with elapsed time in the present embodiment. The cells are cells having the differentiation potency into the cardiac muscle at the initial stage in the present embodiment. The cells include cells differentiated from stem cells such as embryonic stem cells or induced pluripotent stem cells. The cells include, for example, ES cells or iPS cells.

The myocardial differentiation marker genes and/or undifferentiated marker genes are, for example, genes which enable the state of the myocardial differentiation of the cells to be determined on the basis of whether or not these genes are expressed. These genes are genes related to the myocardial differentiation, and their expression varies before the start of differentiation, along with the advance of differentiation, and/or after the completion of differentiation. These marker genes are preferably genes inherent in the target cells. These marker genes may be homologue genes of an organism different from the organism from which the target cells are derived. For example, the genes may be marker genes having functions equivalent to those of human genes in the mouse cells, or marker genes having functions equivalent to those of mouse genes in the human cells.

The myocardial differentiation marker genes are, for example, genes which expresses specifically in cardiac muscle cells or specifically when the cells differentiate into cardiac muscle cells. The myocardial differentiation marker genes include, for example, cTnT, GATA4, and NCX1. The undifferentiated marker genes are, for example, genes which are expressed in a state where stem cells are undifferentiated. The undifferentiated marker includes undifferentiated marker genes such as Nanog and Tcf3.

The myocardial differentiation marker genes and/or undifferentiated marker genes are, for example, designed so that the expression of luminescent protein is promoted depending on the expression of these genes. For example, in nucleic acid of cells, genes of luminescent protein can be disposed in the downstream of a transcription factor binding site for these marker genes. In this case, the transcription factor to originally control the expression of the marker genes is bound to this transcription factor binding site, and the expression of the genes of luminescent protein are thereby promoted.

The luminescent protein means an enzyme which catalyzes a chemical reaction that produces light without depending on optical energy resulting from illumination light, and the luminescent protein functions as reporter genes when it is introduced in certain genes in cells. One example of the luminescent protein is luciferase. Luciferase catalyzes an oxidative reaction of luciferin which is a substrate when an ATP is present. At the time of this reaction, luciferin emits light.

Luciferase may be derived from various organisms such as fireflies and bacteria. Luciferase can be, for example, Emerald Luc luciferase that generates green light, CBR luciferase that generates red light, and Renilla luciferase that generates blue light. The genes of these luciferases may be commercially available genes. Examples of commercially available vectors which contain luciferase genes include Emerald Luc vector (Toyobo), CBR vector (Promega), Renilla vector (Promega), and NanoLuc vector (Promega).

Introducing the reporter genes of luminescent protein configured to emit light according to the expression of the myocardial differentiation marker genes includes, for example, introducing, into cells, nucleic acid including the transcription factor binding site of the marker genes and also including the genes of the luminescent protein located in the downstream of this site, as described above. More than one set of the transcription factor binding site of the marker genes and luminescent protein may be used. When more than one set are used, these sets may be different from each other.

As shown in step S2, the method according to the present embodiment includes keeping cells alive, and imaging light emitted from the cells in a light shielding state where illumination light and external light are shielded, thereby acquiring a luminescence image. That is, the cells are kept alive after marked. In this state, the luminescence image is acquired. That the cells are kept alive means that, for example, the cells are not fixed. Preferably, the cells are kept differentiatable. The cells are also made restorable to the undifferentiated state. Specifically, cells are cultured in culture medium to which, for example, LIF, Dorsomorphin C, or Cycrosporine A are added. Alternatively, cells are cultured under a condition in which differentiation is inhibited, for example, cultured in culture medium to which an inhibitor of differentiation is added. Acquisition conditions of the luminescence image are: regarding the lower limit value of the variation of the expression of genes to be analyzed, imaging sensitivity at which the amount of bioluminescence generated by an enzyme reaction of, for example, luciferase as luminescent protein can be detected; and a relatively long exposure time which allows background to be significantly distinguished in accordance with the imaging sensitivity. Moreover, to conduct a highly quantitative analysis, it is preferable to use a luminescence imaging system which obtains a clear luminescence image in the shortest possible time so that an image analysis may be easier. The exposure time to acquire a luminescence image is selected from, for example, 1 minute to 60 minutes, and a luminescence image may be acquirable in an exposure time of several seconds to one minute in a genetic analysis having a high expression level. In contrast, in a genetic analysis having a low expression level and/or having a small variation of expression level, a luminescence image may be acquired in an exposure time of 30 to 90 minutes. The variation of the gene expression level is generally compared with time for a long period of several hours to several weeks, so that, for example, even a still image obtained in an exposure time of 10 minutes or more provides a comparable and satisfactory analytic image. Regarding binning, 1×1 (without pixel shift) is preferable, but pixels may be increased in a pseudo-manner, for example, by 2×2 or 4×4.

Bioluminescence is imaged with time, and more than one still image can be acquired. In the present embodiment, an image obtained by imaging bioluminescence generated from at least one cell is referred to as a luminescence image. The luminescence image includes an area derived from luminescent cells where luminescence signals have been detected, and an area derived from nonluminous cells and parts having no cells where no luminescence signals are detected. Therefore, luminescence can be estimated units of one cell or one colony. The acquisition of more than one luminescence image with time permits the analysis of an abnormality in which the motion of the cardiac muscle varies in response to a stimulus by, for example, a drug or a heart disease. A multiwell container such as a microwell plate or more than one dish may be used together to acquire luminescence images for a large number of samples. By conducting more than one observation in parallel, it is possible to compare and assess an influence of any additive such as a chemical compound, a growth factor, or siRNA, and concentration dependence of the additive. It also becomes possible to consider experimental reproducibility by using more than one reaction container.

Imaging can be performed by use of an apparatus including, for example, a filter which mainly transmits light having a certain wavelength corresponding to luminescence, an image pickup device which converts the light into an electric signal, and processing means for creating a luminescence image from the electric signal. An example of the apparatus to acquire a luminescence image is a luminescence imaging system. The luminescence imaging system includes, for example, a bioluminescence imaging system LV200 (manufactured by Olympus Corporation).

As shown in step S3, the method according to the present embodiment can further include acquiring a bright-field image of cells. The bright-field image is, for example, an image obtained by imaging light generated when illumination light applied to stem cells is reflected by the stem cells and/or penetrates the stem cells. That is, the positions and forms of stem cells can be observed without regard to luminescence. The bright-field image includes a phase-contrast image and a differential interference observation image (DIC observation image). The bright-field image can be acquired by substantially the same timing as the acquisition of the luminescence image. Alternatively, the bright-field image can be acquired by any timing independently of the acquisition of the luminescence image. The bright-field images may be sequential images as movies.

As shown in step S4, whether imaging is repeated is determined, and imaging can be performed with time. That is, imaging can be sequentially performed at any intervals. For example, imaging can be performed at intervals of 1 minute to 1 hour. The time of one imaging can be set to any time. The time of one imaging can be adjusted so that a satisfactory luminescence signal may be detected. Obtaining still images at predetermined time intervals in this way can also be referred to as interval imaging.

As shown in step S5, the method according to the present embodiment can further include analyzing the change in the luminescence intensity on the basis of the luminescence image after the acquisition of the luminescence image so that the state of the differentiation of cells can be identified. That is, the change in the luminescence intensity can be read from more than one luminescence image, and converted into a representation form such that the differentiation state can be identified. For example, the change in the luminescence intensity can be visually recognizably represented. For example, the luminescence intensity at a measurement point can be recorded together with its measurement time, and arranged as a table. Alternatively, the luminescence intensity at a measurement point can be plotted on an elapsed time-luminescence intensity plane, and the variation of the luminescence intensity can be thereby represented as a graph.

When the change in the luminescence intensity is read from more than one luminescence image, this change can be read cell by cell. For example, a cell to read is selected in one luminescence image, and the same cell is then also selected from other luminescence images so that the change in the luminescence intensity can be read. Such a selection can be made, for example, by use of a program which is performed on a computer. In this case, in one luminescence image, a region including the cell is surrounded by a square or surrounded freehand so that a region of interest (ROI) is specified. This region of interest is also tracked in the other images. Regarding the specified region, the luminescence intensity is converted into a numerical value by use of the program on the computer, and recorded. More than one ROI may be selected in one luminescence image.

As shown in step S6, the method according to the present embodiment can further include determining the state of the differentiation of cells. The expression of the genes in one or more selected regions can be analyzed as the change in the luminescence intensity. The luminescence intensities in the selected regions may be compared to compare the changes of the luminescence intensities cell by cell or region by region. When the expression of different genes is analyzed, the luminescence intensities of the respective luciferases may be compared by use of, for example, red and green luciferases different in color as markers of the respective genes to detect the difference of expression levels of the respective genes. The luminescence intensities of different luciferases may be observed with time to analyze the variation of the ratio of the respective gene expressions.

The method according to the present embodiment can include determining the relation between the state of the myocardial differentiation and the expression level of the myocardial differentiation marker genes and/or the undifferentiated marker genes from information regarding the induction of differentiation into visualized cardiac muscle cells. In this method, a relational expression between the state of differentiation and the expression level of the marker genes can be obtained on the basis of the obtained information. Further, the state of differentiation in which a certain expression level is indicated can be specified from such a relational expression. A bright-field image of cells may be utilized to determine the state of the differentiation of cells.

According to the present embodiment, for example, the following advantageous effects can be obtained. According to this method, it is possible to observe, in living cells, gene expression in stem cells such as ES cells and iPS cells. The cells are observed alive so that the process of gene expression at the time of differentiation into cardiac muscle cells can be observed.

In this instance, high quantitativity can be obtained since an observation is performed by use of luminescence imaging. It is also possible to observe gene expression in the process of differentiation from stem cells into cardiac muscle cells with time for a long time. In this method, it is possible to visualize a cell-by-cell state regardless of the variation of the state in the cell group by conducting an observation cell by cell. Since a luminescence observation is conducted, a quantitative analysis can be conducted even in a specimen having strong autofluorescence such as an embryoid body. It is possible to more precisely observe cells for a longer time with less damage to cells according to the present method than in an observation using fluorescence which has phototoxicity resulting from the application of excitation light.

More information can be acquired when gene expression is observed as in the present method than when differentiation into cardiac muscle cells is analyzed, for example, by observing beating alone.

In this method, since a bright-field image is acquired to check the positions of cells that emit light, the state of cells which cannot be determined only from a luminescence image can be checked. For example, it is possible to check whether or not cells are present in a region to be observed. It is also possible to check whether the cells being observed are, for example, alive or dead. It is also possible to check whether the cells are at the stage of dividing. There is a possibility that cells may move due to differentiation. When a cell divides into two, the amount of luminescent protein included in one cell may temporarily decrease, or when a cell divides in height direction, cells may be shifted from a focal position and a luminescence signal may be reduced. It is difficult to determine the state of such cells only by the luminescence image. Thus, analyzing the state of the differentiation on the basis of the bright-field image is important. Acquiring the bright-field image in this way reinforces the effectiveness of the luminescence image.

In this method, cells differentiated from stem cells including at least embryonic stem cells (ES cells) or induced pluripotent stem cells (iPS cells) are targeted for observation, so that it is possible to obtain information regarding differentiation which is important in the application to, for example, regenerative medicine.

It is possible to discriminate, for example, each process of differentiation by using more than one marker. In this instance, the degree of freedom in the design of an experimental system is higher when luminescence is used than when fluorescence is used.

According to the analysis included in the present method, the state of the differentiation of cells can be precisely determined. Such information can accelerate the elucidation of the mechanism of the myocardial differentiation of stem cells, and the application to myocardial regenerative medicine.

In the present method, when the analysis of the beating of cells, the analysis of the calcium concentration, and the analysis of cellular electrical potential are further included, information amount to be acquired increases, and more information regarding the differentiation of the cells into the cardiac muscle cells can be obtained.

The present method includes the acquisition of bright-field sequential images as movies, and can further include analyzing motions such as the beating of cells on the basis of the movies. Methods of analyzing the motion of an object on the basis of an image are generally known. Various methods for such motion analyses are known in the art. For example, an optical flow often used in the field of computer vision and a correlational analysis often used in the analysis regarding hydrodynamics are known. In the correlational analysis, a flow velocity of a substance is obtained from the calculation of the correlation function of an image. Such a method is called an image correlation method.

The image correlation method includes a method of calculating an autocorrelation function of a double-exposure image in the same image pickup device, and a method of calculating a cross-correlation function of two images obtained at different times. Since it has become easier to acquire images at high speed owing to the improvement of image pickup devices, the method using the cross-correlation function is the mainstream.

For example, Weisman et al. have developed spatiotemporal image correlation spectroscopy (STICS) to analyze the migration of scaffolding protein associated with cell migration (B. Hebert et al. (2005), "Spatiotemporal image correlation spectroscopy (STICS) theory, verification, and application to protein velocity mapping in living CHO cells", Biophys. J. 88, 3601-3614, which is incorporated herein by reference.). For example, an image correlation method such as STICS detects migration of shades in an image, so that even an image of cells having unclear edges can be targeted for analysis. This is particularly advantageous to targeting cells or others for analysis, compared to an analysis such as the optical flow that uses feature points.

STICS is briefly described. STICS described here is an example of an image correlation method, and may be suitably altered, or some other method including processing to find the correlation between images may be used. For the purpose of explanation, space coordinates x and y and time coordinates t of sequential images are treated as integers. The actual position of the sample and the actual exposure time can be easily obtained by multiplying the space coordinates x and y and the time coordinate t by proportionality coefficients which are determined from optical magnification and exposure intervals. Although the analysis object described here is a two-dimensional image, the analysis object can be easily expanded to a three-dimensional image having volumetric information.

The sample is imaged at given time intervals with an image size of M×M pixels to acquire N sequential images as movies. An image correlation calculation is performed regarding a pair of images having time intervals τ selected from the N sequential images. Image correlation calculations are performed regarding (N−τ) pairs of images selected from the N sequential images. An averaged correlation image which is an average of (N−τ) correlation images obtained by the image correlation calculations is then obtained. The averaged correlation image can be obtained by adding image data at a corresponding pixel position in each correlation image and obtaining an average value.

The above processing is represented by a numerical expression as follows. An average image correlation is represented by Expression (1):

$$R(\xi, \eta; \tau) = \frac{1}{N-\tau} \sum_{t=0}^{N-\tau-1} \frac{\langle \delta I(x, y; t) \delta I(x+\xi, y+\eta; t+\tau) \rangle}{\langle I(x, y; t) \rangle \langle I(x, y; t+\tau) \rangle}, \quad (1)$$

where I(x,y;t) is the signal intensity of an image at coordinates (x,y) acquired at time t.

Here, δI(x,y;t) is a fluctuation value of the signal intensity, and is represented by Expression (2):

$$\delta I(x,y;t) = I(x,y;t) - \langle I(x,y;t) \rangle. \quad (2)$$

<I(x,y;t)> in Expression (1) and Expression (2) indicates averaging of image data over x and y of the image having a size of M×M pixels. That is, <F(x,y;t)> is defined as a function F of x,y,t, as represented by Expression (3):

$$\langle F(x, y; t) \rangle = \frac{1}{M^2} \sum_{x=0}^{M-1} \sum_{y=0}^{M-1} F(x, y; t). \quad (3)$$

When the periodic boundary condition is satisfied with regard to x and y, that is, when F(x+nM,y+mM;t)=F(x,y;t) is satisfied with regard to the integers n and m, the cross-correlation function described in the numerator of Expression (1) can be calculated fast by use of Fourier transform.

To sensitively capture the migration of a gene expression distribution in the sample with time, immobile components in a time section to be analyzed or low-velocity components can be removed in advance. As in a removal method described by B. Hebert et al. (2005), low-frequency components of signal intensity changes may be removed at each coordinate. Stationary components may be removed. That is, a migration component $I_{mov}$ is calculated by Expression (4), and $I_{mov}$ may be used instead of I(x,y;t) in Expression (1).

$$I_{mov}(x, y; t) = I(x, y; t) - \frac{1}{N} \sum_{t=0}^{N-1} I(x, y; t). \quad (4)$$

Next, an analytic method using the averaged correlation image is described. When a distribution image in the sequential images moves in a certain direction with time, an averaged correlation image R (ξ,η;τ) obtained by the aforementioned method is a distribution image having the maximum value at a position located off the center of the image. One method of determining the position of this maximum value is to suppose a Gaussian distribution, i.e., the maximum value is determined by Gaussian fitting to a cross-correlation image.

That is, a Gaussian function represented by Expression (5) is applied to the averaged correlation image by a least squares method using A, β, p, q, and C as variable parameters.

$$F(x,y) = A\exp[-\beta\{(x-p)^2 + (y-q)^2\}] + C. \quad (5)$$

Parameters p and q obtained by the application are maximum positions ($p_\tau$, $q_\tau$) of the averaged correlation image at the time intervals $\tau$. Therefore, the maximum positions ($p_\tau$, $q_\tau$) of the averaged correlation image are determined for each delay time $\tau(=1$ to $N-1)$.

A migration velocity ($v_x$, $v_y$) of the distribution in the image is determined as a proportionality coefficient $v_x$, $v_y$ of the maximum positions represented by Expression (6) and the delay time.

$$\begin{cases} p_\tau = v_x \tau, \\ q_\tau = v_y \tau. \end{cases} \quad (6)$$

To derive statistically precise $v_x$ and $v_y$, the proportionality coefficients $v_x$ and $v_y$ may be calculated by a regression analysis using the least squares method or the like.

When the above analysis is conducted on the image in a partial region of m×m pixels included in the whole image of M×M pixels, a local migration velocity in this partial region can be derived. That is, an image correlation is calculated for a partial region $A_i$ in which x is in the range of $x_i$ to $x_i+m-1$ and in which y is in the range of $y_i$ to $y_i+m-1$, and a migration velocity for this partial region can be determined. A distribution of migration velocities can be obtained by detecting local migration velocities for a large number of partial images.

A migration velocity at the point of time t can be derived by taking a time section comprising most recent n images with respect to time t from images acquired at different exposure times and conducting the above analysis. That is, image cross-correlation is calculated for images in which t is in the range of $t_i$ to $t_i+n-1$, and can be determined as, for example, a migration velocity at a median time of this time section $t=t_i+(n-1)/2$. By determining a migration velocity using this time section which is continuously or discretely shifted, the changes in migration velocity can be recognized, and the time-dependent change of the migration velocity can be analyzed.

By displaying the migration velocity obtained by the above analytic method on a screen, the result can be visualized, and a user can visually understand the result. A possible display method is to, for example, display a value representing a velocity vector over the sequential images. The value representing the velocity vector includes an arrow which has a length proportional to the magnitude of the migration velocity and which has a head indicating the direction of the vector. The color of the arrow can be displayed in accordance with the magnitude of the velocity.

When an analysis is conducted in the partial region in the image and the migration velocity of a local gene expression distribution is analyzed, a velocity distribution can be visualized by displaying a vector in the center of each partial region. When an analysis is conducted with time, how the migration velocity changes with time can be visualized by displaying the velocity vector at time t over an image at time t.

By conducting the above motion analysis, beating of cells which have differentiated into the cardiac muscle can be analyzed. That is, according to this motion analysis, the functional expression of cells can be analyzed. In the present method, a luminescence image and bright-field sequential images (which are movies) can be acquired for the same sample at the same time. Here, the same time does not mean exactly the same time in a physical point of view, but means the same time in a biological point of view, that is, the same period which can be regarded as the same time even when there is a difference of several minutes or so. Since the luminescence image and the bright-field sequential images (which are movies) can be acquired for the same sample at the same time, differentiation from stem cells into cardiac muscle cells can be analyzed in detail in terms of both gene expression and functional expression.

Although STICS is described here, not only STICS but also various image correlation methods can be used, and various motion analysis methods such as the optical flow may also be used.

A method of analyzing the function of the cardiac muscle is, for example, to measure cellular electrical potential by use of multielectrode arrays. However, such a method of measuring potential goes no further than a local measurement in parts where electrodes are provided, and does not make it possible to acquire information regarding the beating part of the cell group. In contrast, according to the method of analysis using the bright-field image, it is possible to acquire biological information such as the migration amounts of the positions of cells and the velocity of beating regarding all the cells in an observation field of view. To successively analyze the image of a beating heart, it is important to execute a sequential image analyzing process including a sequential image acquiring process to image at an exposure time faster than the upper limit of the motion velocity of the cardiac muscle as a target, and an image calculating process to compare obtained sequential images with time to calculate the migration velocity of each image. An image pickup device and image processing software to execute this sequential image analyzing process are generally available. For example, AQUACOSMOS sold by Hamamatsu Photonics can be used as the image processing software. The kinds of images to be acquired to execute the sequential image acquiring process include a transmission image as a bright-field image resulting from illumination light such as laser, a reflection image, a phase-contrast image, and a differential interference image. Instead of the bright-field image, a fluorescence image obtained by the application of excitation light may be subjected to a sequential image analysis, or the bright-field image and the fluorescence image may be used together to increase fast biological analytic items. It is preferable that the imaging time and imaging intervals as exposure conditions of movies in the sequential image acquiring process be selected from, for example, a range of 10 to 800 ms, and that the beating of the cardiac muscle be set to, for example, a range of 100 to 200 ms. The present invention is not limited to genetic analysis related to the reproduction of the cardiac muscle, but is also applicable to genetic analysis of diseases (e.g. myocardial infarction) related to the abnormality of the beating of the heart.

Thus, the present invention can be the first method which acquires both sequential images and a still image from the same cell or a subject including the image of this cell, associates pieces of information obtained from both the images, and thereby clarify the relation between a functional analysis of the cardiac muscle moving fast and the gene expression level varying slowly.

Figure 2:
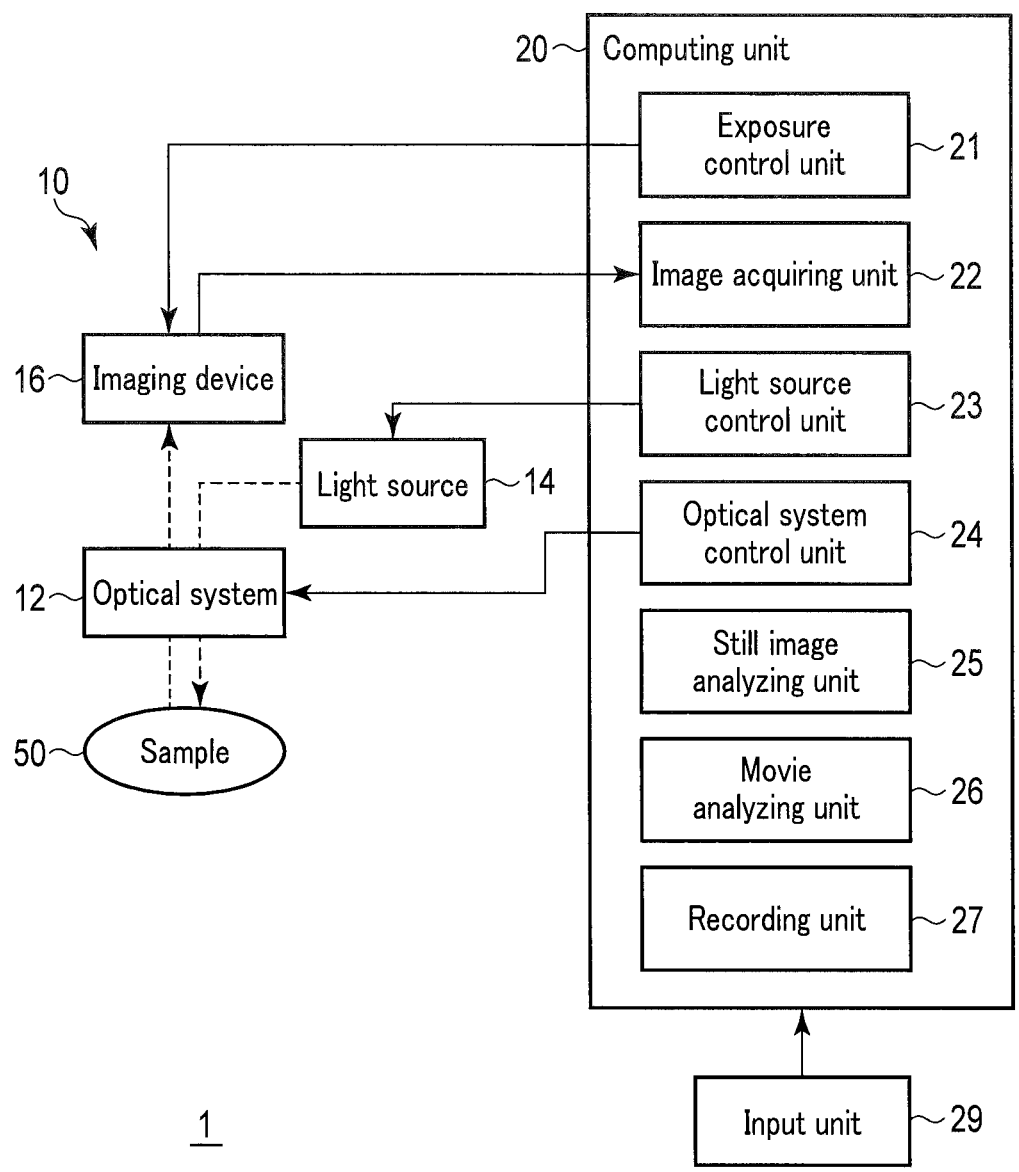
FIG. 2 is a diagram showing an overview of a configuration example of a system capable of simultaneously conducting an analysis of gene expression based on a luminescence image and an analysis of functional expression based on bright-field sequential images according to one embodiment.

An overview of a system capable of simultaneously conducting an analysis of gene expression based on a luminescence image and an analysis of functional expression based on movies that are bright-field images as above is shown in FIG. 2. As shown in FIG. 2, this analytic system 1 comprises a microscope 10 housed in a housing (not shown) in a light-shielding state, a computing unit 20 such as a personal computer capable of performing various computations, and an input unit 29 such as a keyboard or a mouse to input an instruction by the user to the computing unit 20.

An optical system 12, a light source 14, and an imaging device 16 are provided in the microscope 10. The optical system 12 includes various lenses and mirrors. The light source 14 emits given illumination light (e.g. white light) necessary to obtain bright-field images, and the light emitted from this light source 14 is applied to a sample 50 such as stem cells via the optical system 12. This sample 50 is housed in a culture chamber so that cells can live preferably in a predetermined culture environment. The imaging device 16 includes an image pickup device such as a CCD image sensor, and generates an image signal related to a microscopic image of the sample 50 via the optical system 12.

The computing unit 20 comprises an exposure control unit 21, an image acquiring unit 22, a light source control unit 23, an optical system control unit 24, a still image analyzing unit 25, a movie analyzing unit 26, and a recording unit 27. The exposure control unit 21 controls the operation of the imaging device 16. The image acquiring unit 22 acquires the image from the imaging device 16, and performs necessary image conversion and others.

The light source control unit 23 controls the operation of the light source 14. The optical system control unit 24 controls the optical system 12. For example, when a bright-field image is acquired, illumination light emitted from the light source 14 is applied to the sample 50 via the optical system 12. Moreover, when a bright-field image is to be acquired, the exposure time is relatively shortened. In contrast, when a luminescence image is to be acquired, illumination light emitted from the light source 14 is shielded, and the sample 50 is not illuminated. Moreover, when a luminescence image is to be acquired, a relatively long exposure time is set.

The still image analyzing unit 25 analyzes a still image such as a luminescence image. The movie analyzing unit 26 conducts an analysis such as the aforementioned motion analysis. The recording unit 27 records, for example, analytic results of the luminescence image, the movies, and the still image, and results of the motion analysis.

According to the above analytic system 1, it is possible to acquire the luminescence image and the bright-field sequential images which are movies for the same sample at the same time as described above. Further, it is possible to analyze differentiation from stem cells into cardiac muscle cells in detail in terms of both gene expression and functional expression on the basis the acquired images. This analytic system can be fortunately achieved in the aforementioned bioluminescence imaging system LV200.

EXAMPLES

Example 1: Investigation of Influence of Autofluorescence in Embryoid Body Derived from Stem Cells Mouse ES cells were used to examine the degree of the influence of autofluorescence when excitation light for the excitation of fluorescent protein was applied to an embryoid body derived from stem cells.

(1) Culture of Mouse ES Cells

For the culture of the mouse ES cells (BRC6, Riken BRC), KO DMEM culture medium (containing 15% of FBS, Penicillin-Streptomycin (SIGMA diluted 100 times), NEAA (SIGMA diluted 100 times), L-Glutamine (final concentration: 2 mM), and 2-mercaptoethanol (final concentration: 0.1 mM)) were used. The mouse ES cells were cultured on a mouse embryonic fibro-blast (MEF cells) whose division was arrested by a mitomycin C treatment.

(2) Formation of Embryoid Body of Mouse ES Cells

The cultured mouse ES cells were washed with PBS, detached by 0.25% Trypsin-EDTA, and then incubated for 4 hours in an incubator at 37° C. with the KO DMEM culture medium. Feeder cells (MEF) were adhered so that the mouse ES cells alone floated. The culture medium including the mouse ES cells was centrifuged to collect the cells, and the cells were resuspended in 1 ml of KO DMEM culture medium or IMDM culture medium (containing 15% of FBS, Penicillin-Streptomycin (SIGMA diluted 100 times), NEAA (SIGMA diluted 100 times), and 2-mercaptoethanol (final concentration: 0.1 mM)). The number of cells in the solution was counted by a cell counter, and a cell suspension was added so that the number of cells was 2500 or 5000 in each well with Lipidure-Coat culture medium (96 Well Round Bottom; NOF Cooperation) to which the IMDM culture medium was added. The cells were cultured at 37° C. for 3 to 7 days to form an embryoid body.

(3) Investigation of Influence of Autofluorescence of Mouse ES Cells

The formed embryoid body was moved to a gelatin-coated 35 mm dish, and incubated overnight at 37° C. so that the embryoid body adhered to the dish surface. Excitation light was then applied by use of an EGFP filter (460-480 nm, 495-540 nm) to observe the degree of the influence of autofluorescence by use of an inverted fluorescent microscope IX70 and a microscopic digital camera DP70 (manufactured by Olympus Corporation).

Figure 3:
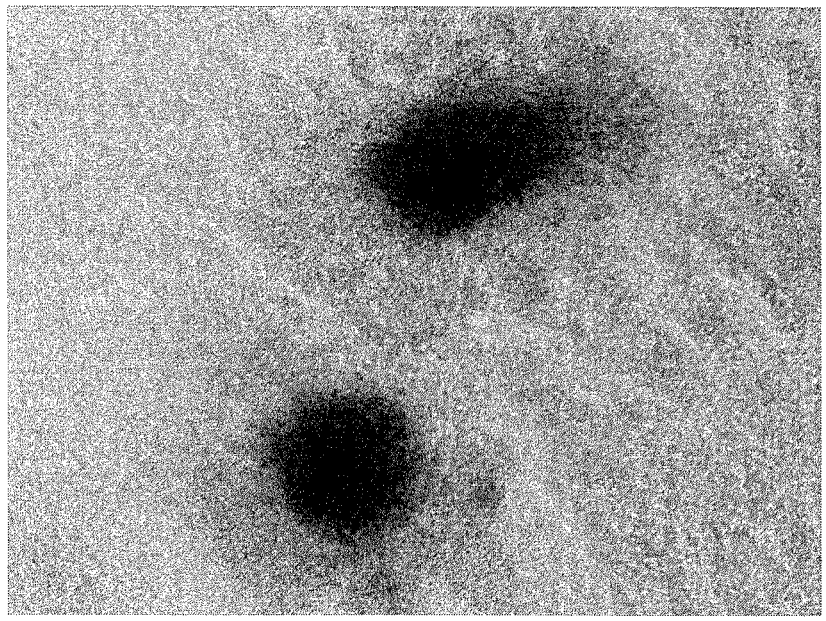
FIG. 3 is an image showing autofluorescence in the case where excitation light for GFP is applied to an embryoid body derived from mouse ES cells, and is a bright-field image.
Figure 4:
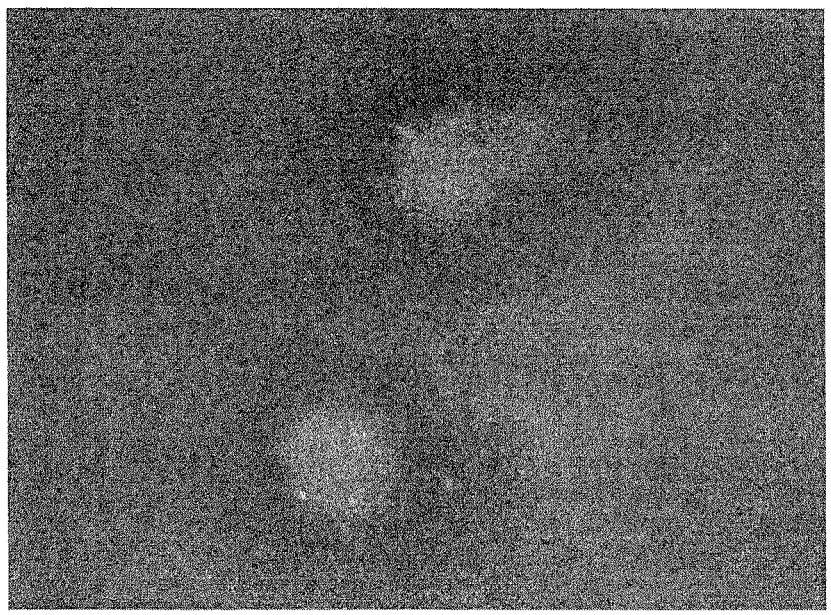
FIG. 4 is an image showing autofluorescence in the case where the excitation light for GFP is applied to the embryoid body derived from the mouse ES cells, and is a luminescence image.

FIG. 3 and FIG. 4 show a bright-field image and a fluorescence image in the case where EGFP excitation light is applied to the mouse ES cells, respectively. It was elucidated by FIG. 3 and FIG. 4 that the embryoid body derived from stem cells had strong autofluorescence. This showed that in a fluorescence observation, autofluorescence had a great influence, and a quantitative analysis was difficult.

Example 2: Expression Analysis of Cardiac Muscle-Specific Marker in Cardiac Muscle Inducing Process of ES Cells and iPS Cells Cardiac troponin T (cTnT) is a protein which expresses specifically in the cardiac muscle. cTnT is utilized as marker genes for myocardial differentiation. The expression of these cTnT genes was used as an index to examine whether the myocardial differentiation inducing process of ES cells and iPS cells can be visualized.

Example 2-1: Analysis of cTnT Expression in Myocardial Differentiation Process of Mouse ES Cells (1) Production of Mouse ES Cells into which Nucleic Acid Including Promoter Region of cTnT Genes and Luciferase Genes was Introduced A promoter region for cTnT genes was cloned with reference to Non Patent Literature "Jin et al., Biochemical and Biophysical Research Communications 1995 Vol. 214, No. 3, p 1168 to 1174", which is incorporated herein by reference, and the promoter sequence was acquired. In this instance, mouse genomic DNA was used as a template. The following two primers were used.

Forward primer 1:
(sequence number 1)
GCCTCGAGTCTAGACTGAGATACAATGCAAAAGCTGG

Reverse primer 1:
(sequence number 2)
GCAGATCTGGTTGAGGGCAGGGCATGGGGAGAGC.

The acquired promoter sequence for cTnT genes was inserted into a neomycin-resistant pGL4.17 luciferase reporter vector (Promega) to produce a "cTnT gene expression specific luminescent vector pcTnT-GL4".

The KO DMEM culture medium was used to culture mouse ES cells (BRC6, Riken BRC) into which the vector was to be introduced. These ES cells were cultured on MEF cells whose division was arrested by a mitomycin C treatment.

A Nucleofection method by Amaxa Nucleofector (Wako Pure Chemical Industries) was used to transfect the pcTnT-GL4 gene expression vector into the mouse ES cells. The transfected cells were cultured overnight in the KO DMEM culture medium together with neomycin-resistant feeder cells, and the culture medium was replaced with KO DMEM culture medium to which an antibiotic G418 (Invitrogen) was added to a final concentration of 250 µg/ml, whereby a selective culture was conducted. In this way, a stably expressing cell line was acquired. These cells will hereinafter be referred to as cTnT-GL4 expression mouse ES cells.

(2) Formation of Embryoid Body of cTnT-GL4 Expression Mouse ES Cells

The cultured cTnT-GL4 expression mouse ES cells were washed with PBS, detached by 0.25% Trypsin-EDTA, and then incubated for 4 hours in an incubator at 37° C. with the KO DMEM culture medium. Feeder cells (MEF) were adhered so that the mouse ES cells alone floated. The culture medium including the mouse ES cells was centrifuged to collect the cells, and the cells were resuspended in 1 ml of KO DMEM culture medium or IMDM culture medium. The number of cells in the solution was measured by a cell counter, and a cell suspension was added so that the number of cells was 2500 or 5000 in each well with Lipidure-Coat culture medium (96 Well Round Bottom; NOF Cooperation) to which the IMDM culture medium was added. The cells were cultured at 37° C. for 3 to 7 days to form an embryoid body.

(3) Myocardial Differentiation Induction of cTnT-GL4 Expression Mouse ES Cells

The formed embryoid body was moved to a gelatin-coated 35 mm dish, and incubated overnight at 37° C. so that the embryoid body adhered to the dish surface. The embryoid body was cultured at 37° C. for about 5 to 14 days to induce its differentiation into beating cardiac muscle cells.

(4) Observation and Analysis of cTnT-GL4 Expression Mouse ES Cells

D-luciferin (manufactured by Wako Pure Chemical Industries) was added to a final concentration of 1 mM to the embryoid body of the cTnT-GL4 expression mouse ES cells which were cultured at 37° C. and came to partly show beating cardiac muscle. The cells were observed in a light-shielding state by use of the bioluminescence microscope LV200 (manufactured by Olympus Corporation) equipped with AQUACOSMOS (Hamamatsu Photonics Corporation) which was an analytic software to analyze beating cells, and a luminescence image was acquired.

The expression of cTnT genes was observed under the following exposure conditions. A CCD camera ImagEM (manufactured by Hamamatsu Photonics Corporation) was used under a condition of binning 1×1. The cTnT-GL4 expression mouse ES cells were imaged for an exposure time of 15 minutes.

Figure 5:
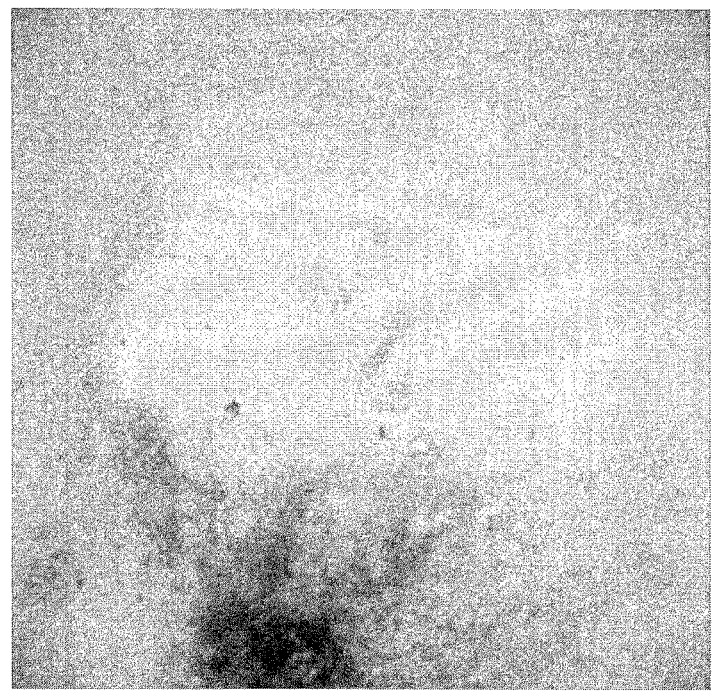
FIG. 5 is an image showing cTnT expression in a process of myocardial differentiation of the embryoid body derived from mouse ES cells into which a reporter vector having luciferase connected to a promoter of cTnT which expresses specifically in the cardiac muscle is introduced.
Figure 6:
FIG. 6 is an image showing cTnT expression in a process of the myocardial differentiation of the embryoid body derived from the mouse ES cells into which the reporter vector having luciferase connected to the promoter of cTnT which expresses specifically in the cardiac muscle is introduced, and is a luminescence image.

A bright-field image of the cTnT-GL4 expression mouse ES cells differentiated into beating cardiac muscle cells is shown in FIG. 5, and a luminescence observation image of the same cells is shown in FIG. 6. As shown in FIG. 5 and FIG. 6, luminescence was confirmed in the beating cardiac muscle cells. That is, the expression of cTnT could be observed by use of luminescence.

Although the stably expressing cell line in which drug resistance genes are introduced for a drug selection is used in Example 2-1, it is also possible to use a transient expression cells. This can be also applied to the following examples.

Example 2-2: Analysis of cTnT Expression in Myocardial Differentiation Process of Mouse iPS Cells (1) Production of Mouse iPS Cells into which Nucleic Acid Including Promoter Region of cTnT Genes and Luciferase Genes was Introduced A promoter region for cTnT genes was cloned with reference to Non Patent Literature "Jin et al., Biochemical and Biophysical Research Communications 1995 Vol. 214, No. 3, p 1168 to 1174", and the promoter sequence was acquired. In this instance, mouse genomic DNA was used as a template. As primers, Forward primer 1 and Reverse primer 1 mentioned above were used.

The acquired promoter sequence for cTnT genes was inserted into a neomycin-resistant pGL4.17 luciferase reporter vector (Promega) to produce a "cTnT gene expression specific luminescent vector pcTnT-GL4".

The KO DMEM culture medium was used to culture mouse iPS cells (iPS-MEF-Ng-20D-17, Kyoto University) into which the vector was to be introduced. These iPS cells were cultured on MEF cells whose division was arrested by a mitomycin C treatment.

A Nucleofection method by Amaxa Nucleofector (Wako Pure Chemical Industries) was used to transfect the pcTnT-GL4 gene expression vector into the mouse iPS cells. The transfected cells were cultured overnight in the KO DMEM culture medium together with neomycin-resistant feeder cells, and the culture medium was replaced with KO DMEM culture medium to which the antibiotic G418 (Invitrogen) was added to a final concentration of 250 µg/ml, whereby a selective culture was conducted. In this way, a stably expressing cell line was acquired. These cells will hereinafter be referred to as cTnT-GL4 expression mouse iPS cells.

(2) Formation of Embryoid Body of cTnT-GL4 Expression Mouse iPS Cells

The cultured cTnT-GL4 expression mouse iPS cells were washed with PBS, detached by 0.25% Trypsin-EDTA, and then incubated for 4 hours in an incubator at 37° C. with the KO DMEM culture medium. Feeder cells (MEF) were adhered so that the mouse iPS cells alone floated. The culture medium including the mouse iPS cells was centrifuged to collect the cells, and the cells were resuspended in 1 ml of KO DMEM culture medium or IMDM culture medium. The number of cells in the solution was measured by a cell counter, and a cell suspension was added so that the number of cells was 2500 or 5000 in each well with Lipidure-Coat culture medium (96 Well Round Bottom; NOF Cooperation) to which the IMDM culture medium was added. The cells were cultured at 37° C. for 3 to 7 days to form an embryoid body.

(3) Myocardial Differentiation Induction of cTnT-GL4 Expression Mouse iPS Cells

The formed embryoid body was moved to a gelatin-coated 35 mm dish, and incubated overnight at 37° C. so that the embryoid body adhered to the dish surface. The embryoid body was cultured at 37° C. for about 5 to 14 days to induce its differentiation into beating cardiac muscle cells.

(4) Observation and Analysis of cTnT-GL4 Expression Mouse iPS Cells

D-luciferin (manufactured by Wako Pure Chemical Industries) was added to a final concentration of 1 mM to the embryoid body of the cTnT-GL4 expression mouse iPS cells which were cultured at 37° C. and came to partly show beating cardiac muscle. The beating cells were observed by use of the bioluminescence microscope LV200 (manufactured by Olympus Corporation) equipped with AQUACOSMOS (Hamamatsu Photonics Corporation). The expression of cTnT genes was observed under the following exposure conditions. The CCD camera ImagEM (manufactured by Hamamatsu Photonics Corporation) was used under a condition of binning 1×1. The cTnT-GL4 expression mouse iPS cells were imaged for an exposure time of 15 minutes.

Figure 7:
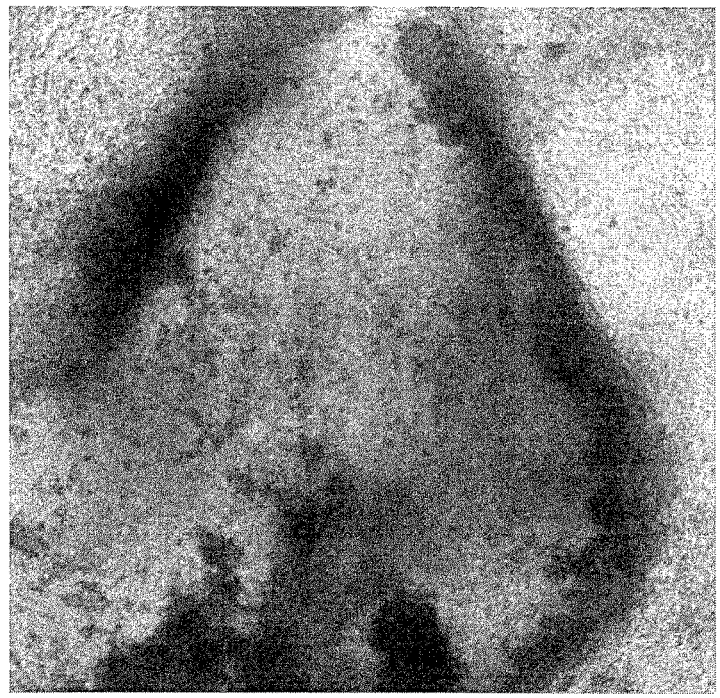
FIG. 7 is an image showing cTnT expression in the process of myocardial differentiation of an embryoid body derived from mouse iPS cells into which the reporter vector having luciferase connected to the promoter of cTnT which expresses specifically in the cardiac muscle is introduced, and is a bright-field image.
Figure 8:
FIG. 8 is cTnT expression in the process of the myocardial differentiation of the embryoid body derived from the mouse iPS cells into which the reporter vector having luciferase connected to the promoter of cTnT which expresses specifically in the cardiac muscle is introduced, and is a luminescence image.

FIG. 7 shows a bright-field image of embryoid body derived cells including the cTnT-GL4 expression mouse iPS cells differentiated into beating cardiac muscle cells. FIG. 8 shows a luminescence observation image of the same cells. As shown in FIG. 7 and FIG. 8, luminescence was confirmed in the cardiac muscle cells derived from the beating iPS cells. That is, the expression of cTnT could be observed by use of luminescence.

Example 2-3: Analysis of Change of cTnT Expression with Time in Myocardial Differentiation Process of Mouse iPS Cells The process of the myocardial differentiation of the cTnT-GL4 expression mouse iPS cells produced in Example 2-2 was observed with time for a long time, and the change of the expression of cTnT was analyzed.

(1) Culture of cTnT-GL4 Expression Mouse iPS Cells

KO DMEM culture medium containing G418 (with a final concentration of 250 μg/ml) was used to culture the cTnT-GL4 expression mouse iPS cells on neomycin-resistant MEF cells whose division was arrested by a mitomycin C treatment.

(2) Formation of Embryoid Body of cTnT-GL4 Expression Mouse iPS Cells and Myocardial Differentiation Induction The cTnT-GL4 expression mouse iPS cells were washed with PBS, detached by 0.25% Trypsin-EDTA, and then incubated for 4 hours in an incubator at 37° C. with the KO DMEM culture medium. Feeder cells (MEF) were adhered so that the cTnT-GL4 expression mouse iPS cells alone floated. The culture medium including the cTnT-GL4 expression mouse iPS cells was centrifuged to collect the cells, and the cells were resuspended in 1 ml of IMDM culture medium. The number of cells in the solution was measured by a cell counter, and a cell suspension was added so that the number of cells was 2500 or 5000 in each well with Lipidure-Coat culture medium (96 Well Round Bottom; NOF Cooperation) to which the IMDM culture medium was added. The cells were cultured at 37° C. for 3 to 7 days to form an embryoid body.

(3) Myocardial Differentiation Induction of cTnT-GL4 Expression Mouse iPS Cells and Analysis of Change of cTnT Expression with Time The formed embryoid body was moved to a gelatin-coated 35 mm dish (containing the IMDM culture medium and luciferin with a final concentration of 1 mM), and incubated 24 hours at 37° C. so that the embryoid body adhered to the dish surface. The culture medium was replaced with new IMDM culture medium (luciferin with a final concentration of 1 mM), and the bioluminescence microscope LV200 (manufactured by Olympus Corporation) equipped with AQUACOSMOS (Hamamatsu Photonics Corporation) was used to conduct a long-term observation of about 5 days. The expression of cTnT genes was observed under the following exposure conditions. The CCD camera ImagEM (manufactured by Hamamatsu Photonics Corporation) was used under a condition of binning 1×1. The cTnT-GL4 expression mouse ES cells were imaged for an exposure time of 10 minutes and at exposure intervals of 15 minutes. In this instance, movie acquisition using an HD recording function of AQUACOSMOS was simultaneously performed at the time of bright-field exposure to observe how the cells differentiated into cardiac muscle cells were beating. The exposure conditions of movies were an exposure time of 124 ms and exposure intervals of 124 ms, and 50 to 100 images were sequentially taken to acquire movies. Obtained data were analyzed by AQUACOSMOS (Hamamatsu Photonics Corporation). For recognition with the taken images, sequential images (movies) sequentially taken at a frame rate higher than the time required for the process of contraction and relaxation are needed. The individual cell position in each frame can be determined manually or by various image recognition methods using frame images at previous and subsequent times as clues. It is also possible to recognize the beating by analyzing the motion of a light-dark pattern of an image in accordance with a method such as an optical flow or an image correlation method without specifying the individual cell position.

Figure 9:
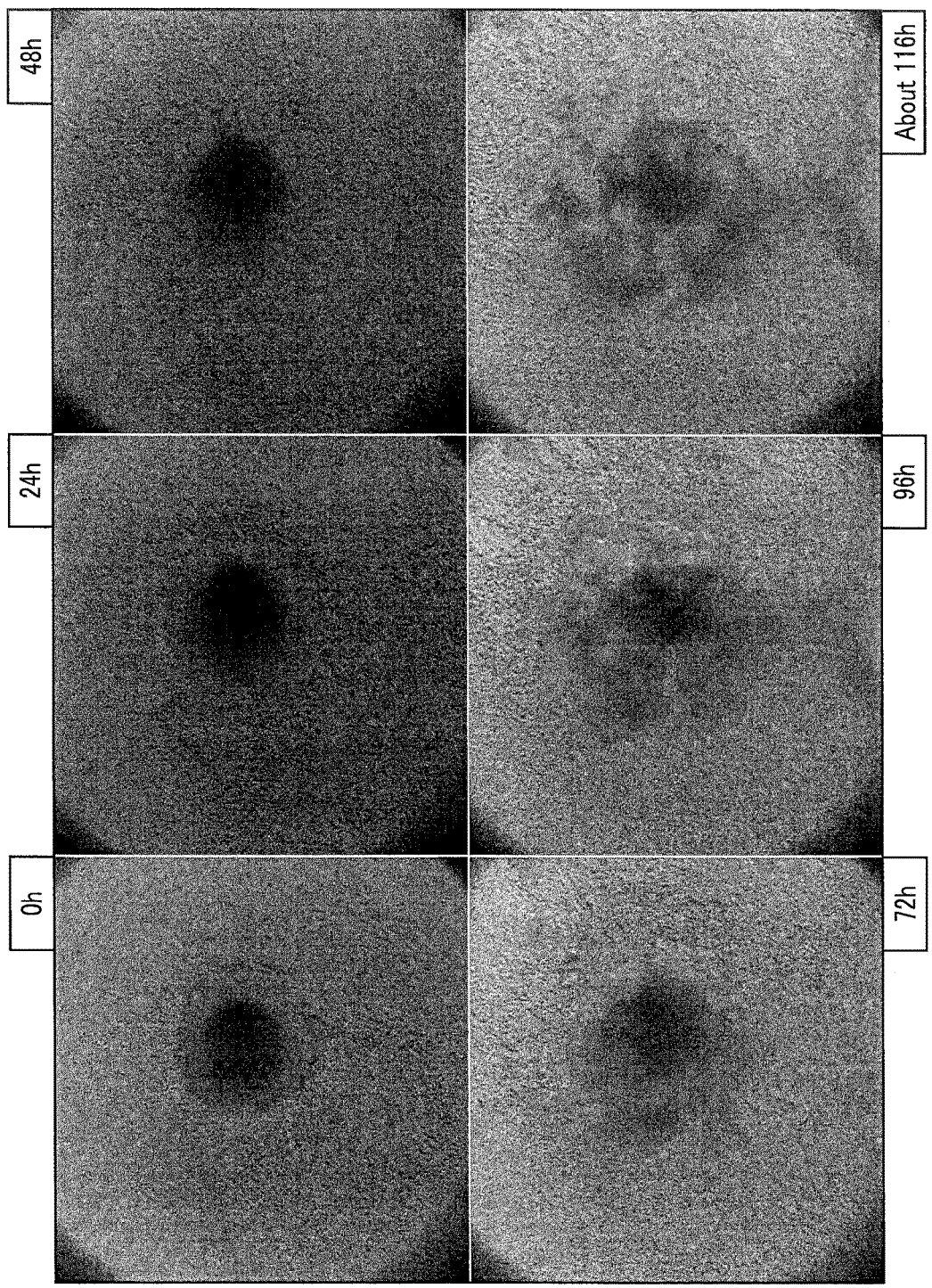
FIG. 9 is a bright-field image in which expression of cTnT in the process of myocardial differentiation of the embryoid body derived from the mouse iPS cells is observed with time.

FIG. 9 shows a bright-field image of a cTnT expression state of the embryoid body derived from the cTnT-GL4 expression mouse iPS cells every 24 hours from the start of observation. FIG. 10 shows a luminescence image of the same embryoid body. FIG. 12 shows a graph in which the change of the luminescent intensity of a ROI in the image of FIG. 11 is analyzed by AQUACOSMOS (Hamamatsu Photonics Corporation). As shown in FIG. 9 and FIG. 10, the expression area of cTnT gradually spreading with elapsed time was observed. The beating of cells in a part in which cTnT was expressed was observed after about 72 hours had passed by the HD recording function. As shown in FIG. 12, the increase of the luminescence intensity of the part surrounded by the ROI with elapsed time and the increase of the cTnT expression with elapsed time were observed.

Example 2-4: Analysis of Beating in Myocardial Differentiation Process of Mouse iPS Cells In the present examples, beating in the myocardial differentiation process of mouse iPS cells was analyzed on the basis of STICS, one of motion analyses made by the image correlation method.

(1) Analytic Method

Bright-field sequential images and luminescence images were acquired in the myocardial differentiation process of the cTnT-GL4 expression mouse iPS cells similar to those used in Example 2-3. Regarding the bright-field sequential images, sequential images of 61 seconds or 74 seconds were acquired every 15 minutes throughout an observation period. The exposure intervals of the images included in the sequential images were 0.61 seconds or 0.37 seconds. An analytic region of horizontal 264 pixels×vertical 256 pixels was extracted from a right central part of the taken image of 512×512 pixels. The extracted analytic region is indicated as region R10 in FIG. 13. Sub regions of 32×32 pixels were filled in the extracted analytic region so that the sub regions are shifted from each other by 8 pixels both vertically and horizontally, and the following motion analysis was conducted in each sub region to quantitatively assess a local motion in the sub region.

In each sub region, a cross-correlation image was calculated regarding two images at $t_n$ and $t_{n+1}$ wherein $t_n$ was the time when the n-th frame of the sequential images was acquired, and its peak position was determined by Gaussian fitting. When the peak position was (p, q), the velocity of the subject at time $t_n$ in this sub region was (p/Δt, q/Δt). Here, Δt is an interval $t_{n+1}-t_n$ of the exposure times of the two images. An actual velocity in the sample can be calculated by multiplying the velocity value by the conversion factor which converts the pixel value to the actual distance and is determined by the magnification of an imaging optical system and the distance between the pixels of the image pickup device.

In each sub region, the standard deviation of displacement of the temporal velocities ($v_x(t)$, $v_y(t)$) obtained per minute calculated as above was defined as beating strength in this point and time region. As the definition of the beating strength, the variance of velocity displacements in a time region or the maximum value of magnitude may be used instead of the definition used this time. The value of the beating strength calculated in the sub region at 8 pixel intervals as above was interpolated in the whole analytic region of 264 pixels×longitudinal 256 pixels by natural neighbor interpolation to draw a beating distribution image.

At the position corresponding to each time of each sub region, the distribution of velocities and temporal changes thereof can be visually recognized when the velocity vectors are drawn as arrows or when the velocity vectors are displayed in different colors depending on the magnitude of the velocities. When this display is superimposed on the corresponding bright-field image or luminescence image, the relation between the state at the relevant position and the velocity can be visually recognized. In the case of the bright-field image, the size and thickness of a cell, the positional relation in the embryoid body or tissue, etc. are cited as the state at the relevant position. In the case of the luminescence image, a gene expression level in a cell in the relevant part, the degree of differentiation and the like are cited as the state at the relevant position.

When an analysis using mutual velocity components between two sub regions is conducted, the relationship of motion between these regions can be assessed. The velocity components include, for example, components having great displacement among horizontal and vertical components for a taken image, and components in directions having great displacement throughout the time region. When a velocity component $v_1(t_n)$ in a first region and a velocity component $v_2(t_n)$ in a second region at time $t_n$ are drawn as a scatter diagram, the degree of synchronization of the motions between two points can be assessed. When the motions at two points are synchronous, points of $(v_1, v_2)$ at each time are arranged on an ascending or descending straight line, and the degree of synchronization can be quantitatively estimated by a parameter obtained from a regression analysis, for example, by the coefficient of determination $R^2$. As the degree of synchronization, an absolute value $|r|$ of a correlation coefficient or a root mean square of the displacement from a straight line model determined by a regression analysis may be used instead.

In addition, a duration time of synchronization can be estimated by calculating a cross-correlation $C_{12}(\tau)=\Sigma_t[v_1(t_n)\cdot v_2(t_n+\tau)]$ of $v_1(t_n)$ and $v_2(t_n)$. A synchronization duration time between regions can be assessed in relation to the continuation time of the motion in each region by comparing an autocorrelation $C_{11}(\tau)=\Sigma_t[v_1(t_n)\cdot v_1(t_n+\tau)]$ in the first region and an similarly-defined autocorrelation $C_{22}$ in the second region with a cross-correlation $C_{12}$, namely by calculating, for example, $C_{12}^2/(C_{11}\times C_{22})$ or its square root.

(2) Analytic Results

Figure 13:
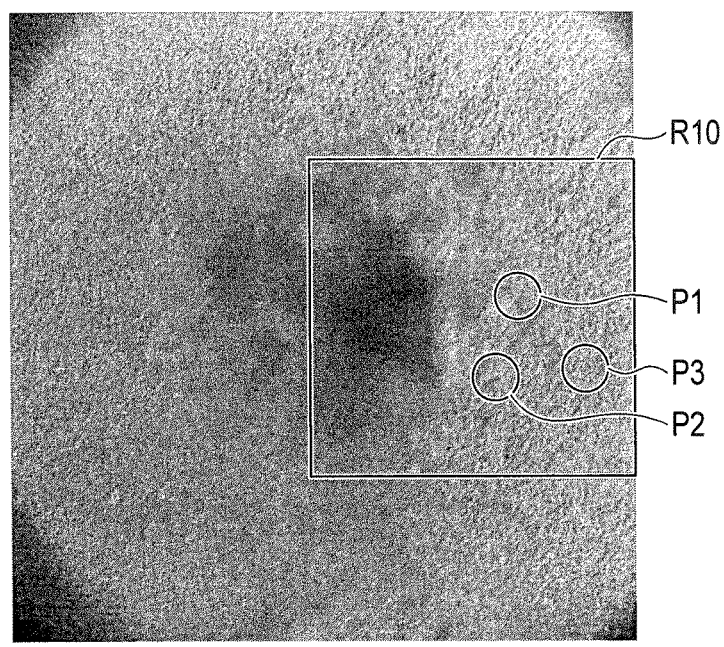
FIG. 13 is a diagram showing an area where beating of cells is analyzed by an image correlation method.

The analytic results in the present examples are described. As described above, the square region R10 included in the image in FIG. 13 shows the region of an image used in the analysis shown in FIGS. 14 to 21 in the present examples 2-4. Three positions indicated by circular marks in FIG. 13 are regions where data targeted for analysis are acquired in the present example 2-4. These regions are referred to as the first point P1, the second point P2, and the third point P3.

Figure 14:
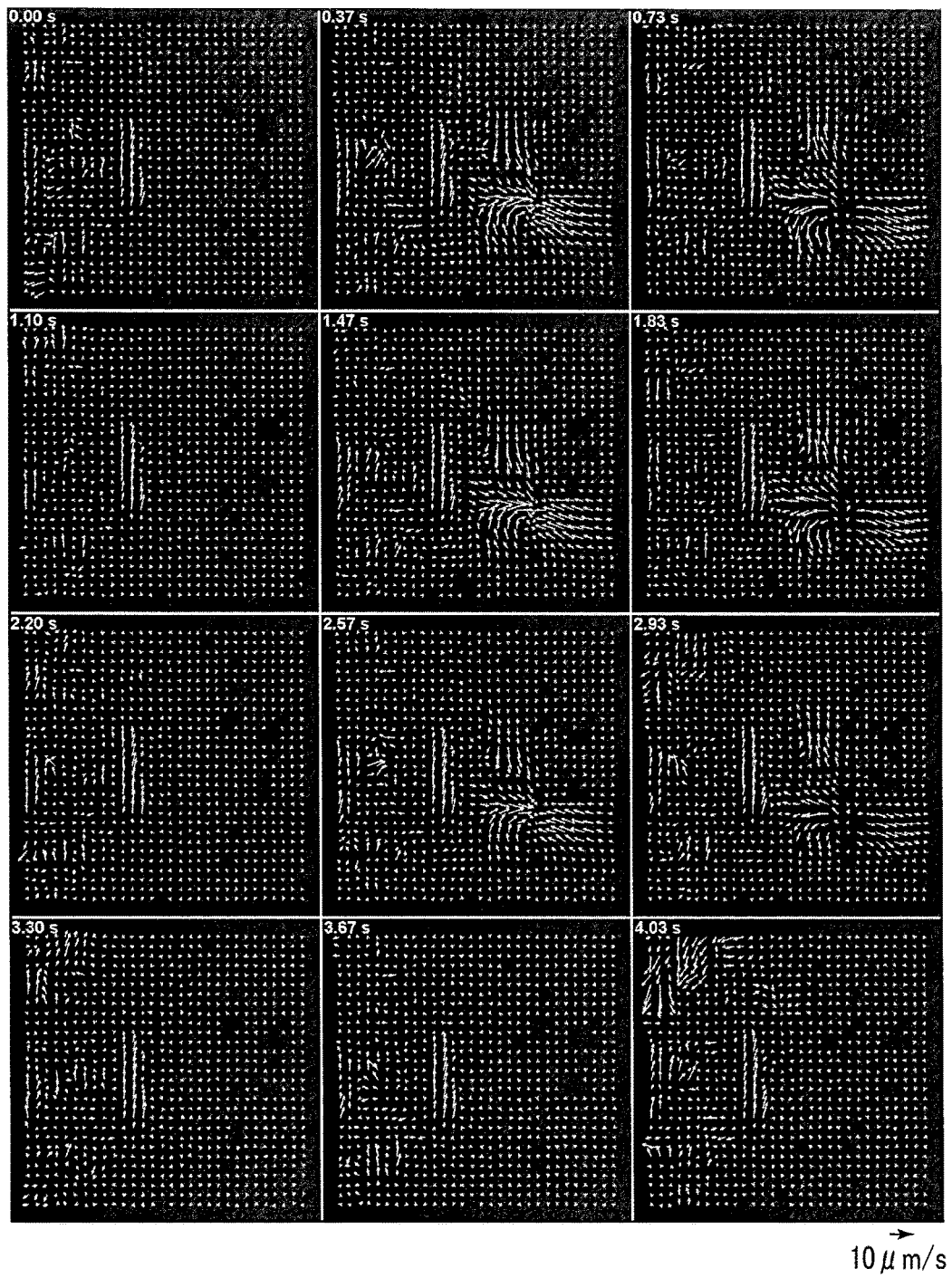
FIG. 14 is a diagram showing a result of an analysis made by the image correlation method using bright-field sequential images after 91 hours from the start of observation.

Results of the STICS analysis using bright-field sequential images which are included in a movie after 91 hours from the start of observation are shown in FIG. 14. The target of the analysis is the region R10 shown in FIG. 13. FIG. 14 shows the velocity of each part by the length of an arrow, each diagram in FIG. 14 showing a result of the analysis in each time section within 4.03 seconds. The elapsed time is indicated in the upper left part of each diagram, and the scale of the length of the arrow is indicated in the lower right part of FIG. 14. As shown in FIG. 14, it is obvious that the velocity and direction of each point change with elapsed time at the first point P1, the second point P2, and the third point P3 shown in FIG. 13, that is, beating occurs at these positions.

The analytic results obtained after 66 hours, 71 hours, 76 hours, 81 hours, 86 hours, and 91 hours from the start of observation are shown in FIG. 15. In FIG. 15, the elapsed time from the start of observation is shown in the first column in which "time after start of observation" is indicated. Each diagram in the second column in which "bright field" is indicated in FIG. 15 shows a bright-field image in each time.

Diagrams in the third column in which "STICS/gene expression" is indicated in FIG. 15 show images in which analytic results of STICS are superimposed on the luminescence images showing cTnT expression acquired by the method shown in the example 2-3 as in the images shown in FIG. 10. Bright parts in the luminescence images are parts where the expression level of cTnT is high. Parts where arrows indicating the results of STICS are long are parts where the velocity is high.

Images in the fourth column of FIG. 15, which are labelled as "beating", represent the beating strength visualized as intensity of pixel values. The beating strength is the standard deviation at each point of the velocity obtained by conducting the STICS analysis on the basis of 100 to 200 images sequentially acquired in 61 seconds to 74 seconds. Higher intensity is shown when the standard deviation is higher. In other words, higher intensity is shown when the change of velocity is greater at each point, that is, when beating is stronger. As apparent from the comparison between the images in the third column and the fourth column in FIG. 15, beating is stronger in regions where the expression of cTnT genes is greater.

The analytic results after 76 hours, 81 hours, 86 hours, and 91 hours from the start of observation are further described in detail. FIG. 16A to FIG. 16G show the analytic results obtained after 76 hours from the start of observation. FIG. 17A to FIG. 17G show the analytic results obtained after 81 hours from the start of observation. FIG. 18A to FIG. 18G show the analytic results obtained after 86 hours from the start of observation. FIG. 19A to FIG. 19G show the analytic results obtained after 91 hours from the start of observation.

The respective left diagrams in FIG. 16A, FIG. 17A, FIG. 18A and FIG. 19A show images representing the analytic results by STICS by arrows that are displayed over bright-field images of cells. The respective right diagrams in FIG. 16A, FIG. 17A, FIG. 18A and FIG. 19A show the standard deviation of velocity obtained by STICS, as in the fourth column in FIG. 15, and represent beating strength by intensity. The STICS results were analyzed regarding the first point P1, the second point P2 and the third point P3 indicated by circular marks in FIG. 16A, FIG. 17A, FIG. 18A and FIG. 19A.

FIG. 16B, FIG. 17B, FIG. 18B and FIG. 19B represent how the velocities at the first point P1 (Point 1), the second point P2 (Point 2) and the third point P3 (Point 3) in each time zone change with time from the start of observation. In each diagram, the horizontal axis indicates the elapsed time (s), and the vertical axis indicates the velocity (μm/s). In each diagram, a broken line indicates the velocity at the first point P1, a gray solid line indicates the velocity at the second point P2, and a dashed line indicates the velocity at the third point P3. Here, the velocities at the first point P1 and the second point P2 indicate velocity components in the vertical direction (y-axis direction) of the image shown, for example, in FIG. 16A, and the velocity at the third point P3 indicates a velocity component in the horizontal direction (x-axis direction) of the image shown, for example, in FIG. 16A. Because displacement in the vertical direction is greater than that in the horizontal direction at both the first point P1 and the second point P2 and because displacement in the horizontal direction is greater than that in vertical direction at the third point P3 after 91 hours from the start of observation, the velocity components in the vertical direction are focused at the first point P1 and the second point P2 and the velocity component in the horizontal direction is focused at the third point P3.

As should be obvious from FIG. 16B, FIG. 17B, FIG. 18B, and FIG. 19B, the maximum value of velocity gradually increased as time elapsed from the start of observation. This means that beating became stronger as time elapsed from the start of observation. It should be also apparent from these drawings that the direction of velocity at the first point P1 is opposite (180 degrees different in phase) to the direction of velocity at the second point P2 and the third point P3 but that the timing of the velocity change is the same at all of the first point P1, the second point P2 and the third point P3. That is, beating is synchronous at all the points.

Figure 16B:
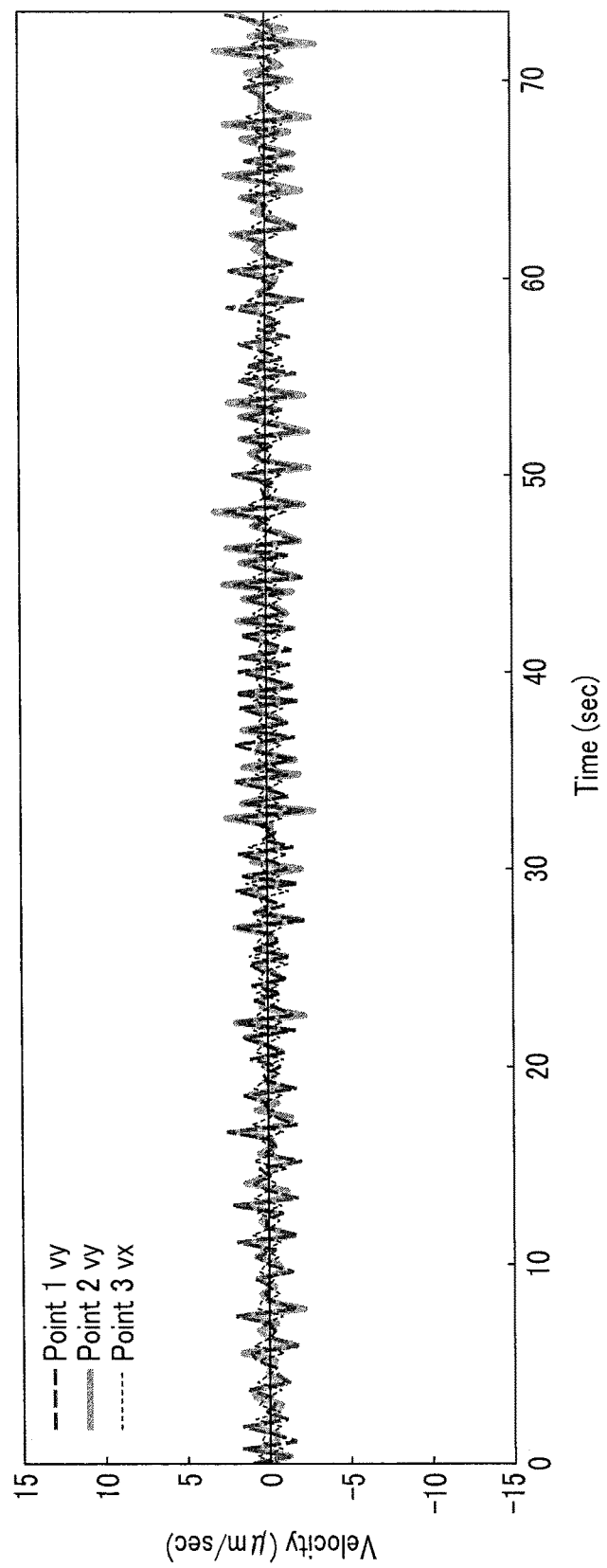
FIG. 16B is a diagram showing how the velocity at each analytic point changes with time after 76 hours from the start of observation.
Figure 16C:
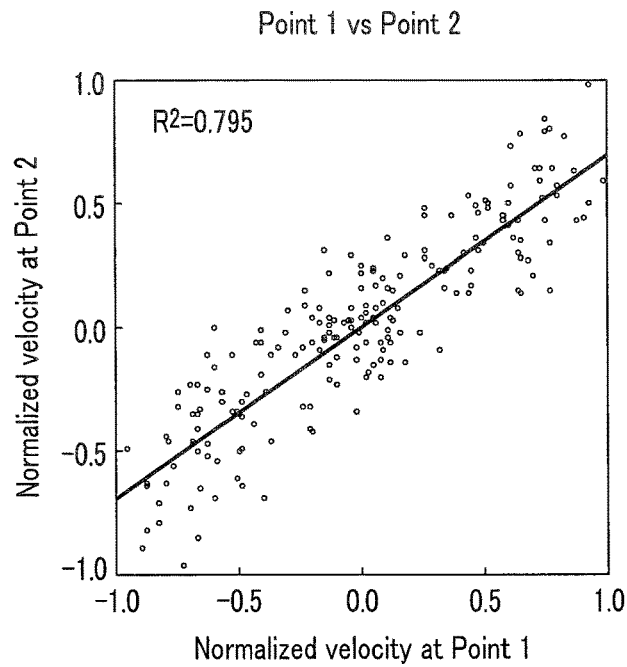
FIG. 16C is a diagram showing how the velocity relation between the first point P1 and the second point P2 is after 76 hours from the start of observation.

The correlation of the velocities at the respective positions was analyzed regarding data obtained 76 hours after the start of observation shown in FIG. 16B. That is, in FIG. 16C, the simultaneously measured velocities at the first point P1 are plotted as the horizontal axis component, and the velocities at the second point P2 are plotted as the vertical axis component. Each point represents one of about 200 data points in the velocity data shown in FIG. 16B. In FIG. 16C, the values are normalized so that the maximum value of velocity is 1. Moreover, a straight line representing linear model regarding the plotted data, and the coefficient of determination $R^2$ which is the square of the correlation coefficient R are shown in FIG. 16C. The coefficient of determination $R^2$ that is closer to 1 represents that the beating at the first point P1 and the beating at the second point P2 are more synchronous.

Figure 16D:
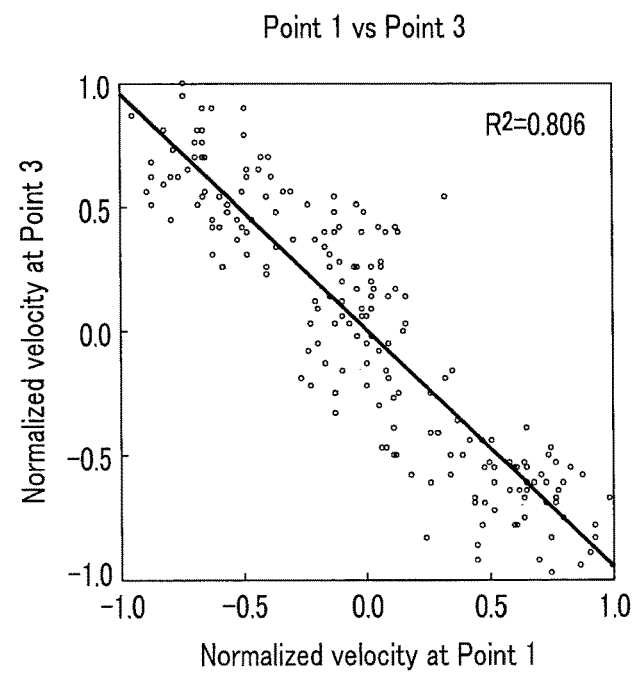
FIG. 16D is a diagram showing the velocity relation between the first point P1 and the third point P3 is after 76 hours from the start of observation.
Figure 16E:
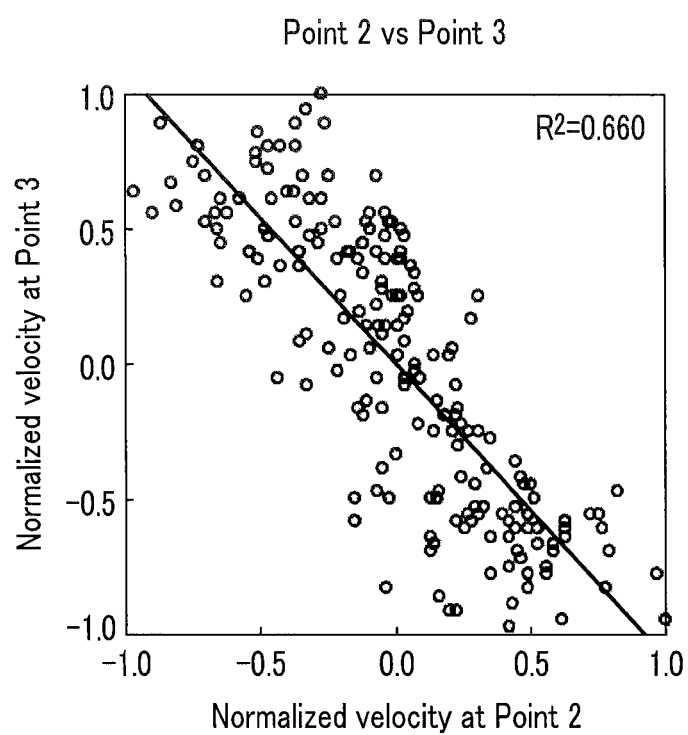
FIG. 16E is a diagram showing how the velocity relation between the second point P2 and the third point P3 is after 76 hours from the start of observation.

Similarly, regarding data obtained 76 hours after the start of observation shown in FIG. 16B, FIG. 16D shows a diagram in which the velocity at the first point P1 is plotted as the horizontal axis component and the velocity at the third point P3 are plotted as the vertical axis component, and FIG. 16E shows a diagram in which the velocity at the second point P2 is plotted as the horizontal axis component and the velocity at third point P3 is plotted as the vertical axis component.

Figure 17B:
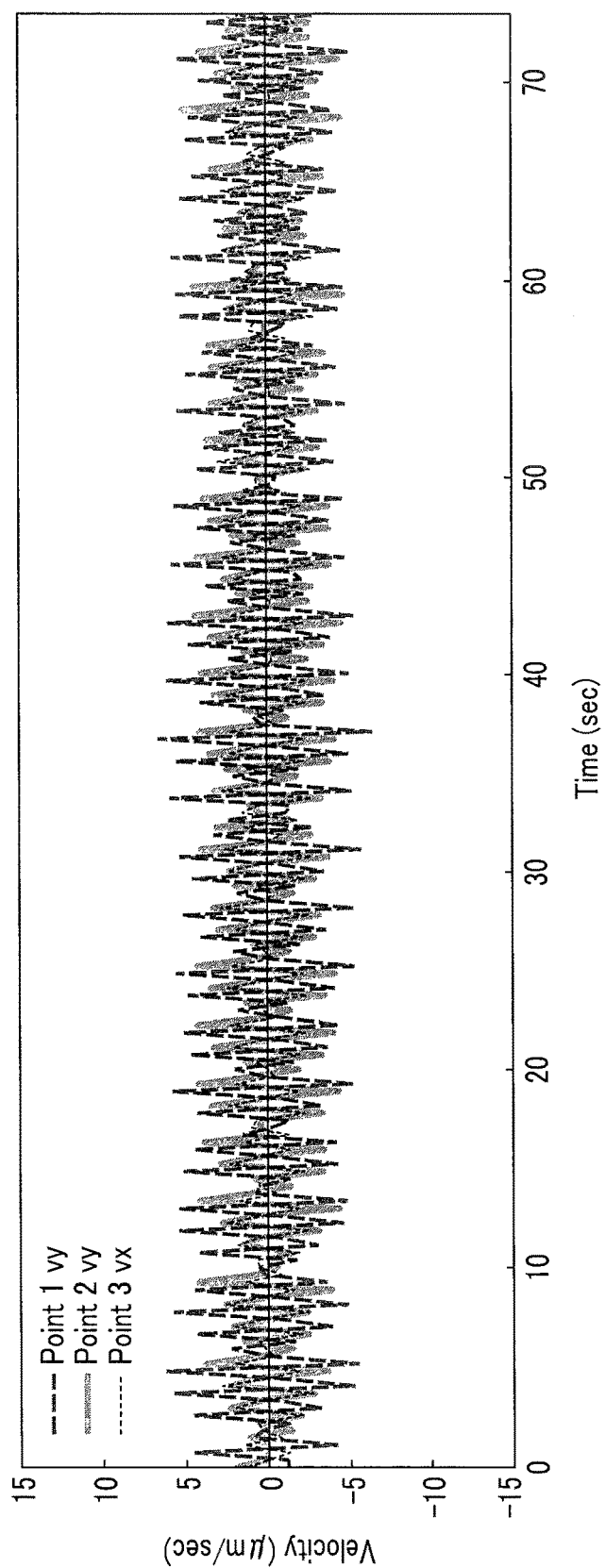
FIG. 17B is a diagram showing how the velocity at each analytic point changes with time after 81 hours from the start of observation.
Figure 17E:
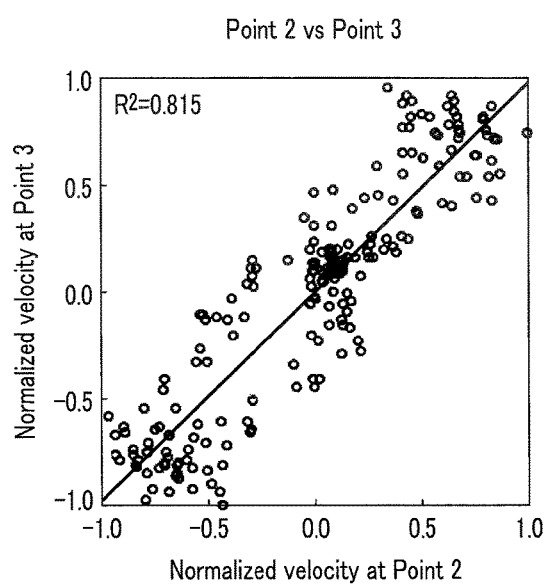
FIG. 17E is a diagram showing how the velocity relation between the second point P2 and the third point P3 is after 81 hours from the start of observation.

Similarly, regarding data 81 hours after the start of observation shown in FIG. 17B, FIG. 17C shows a diagram in which the velocity at the first point P1 is plotted as the horizontal axis component and the velocity at the second point P2 is plotted as the vertical axis component, FIG. 17D shows a diagram in which the velocity at the first point P1 is plotted as the horizontal axis component and the velocity at third point P3 is plotted as the vertical axis component, and FIG. 17E shows a diagram in which the velocity at the second point P2 is plotted as the horizontal axis component and the velocity at third point P3 is plotted as the vertical axis component.

Figure 18B:
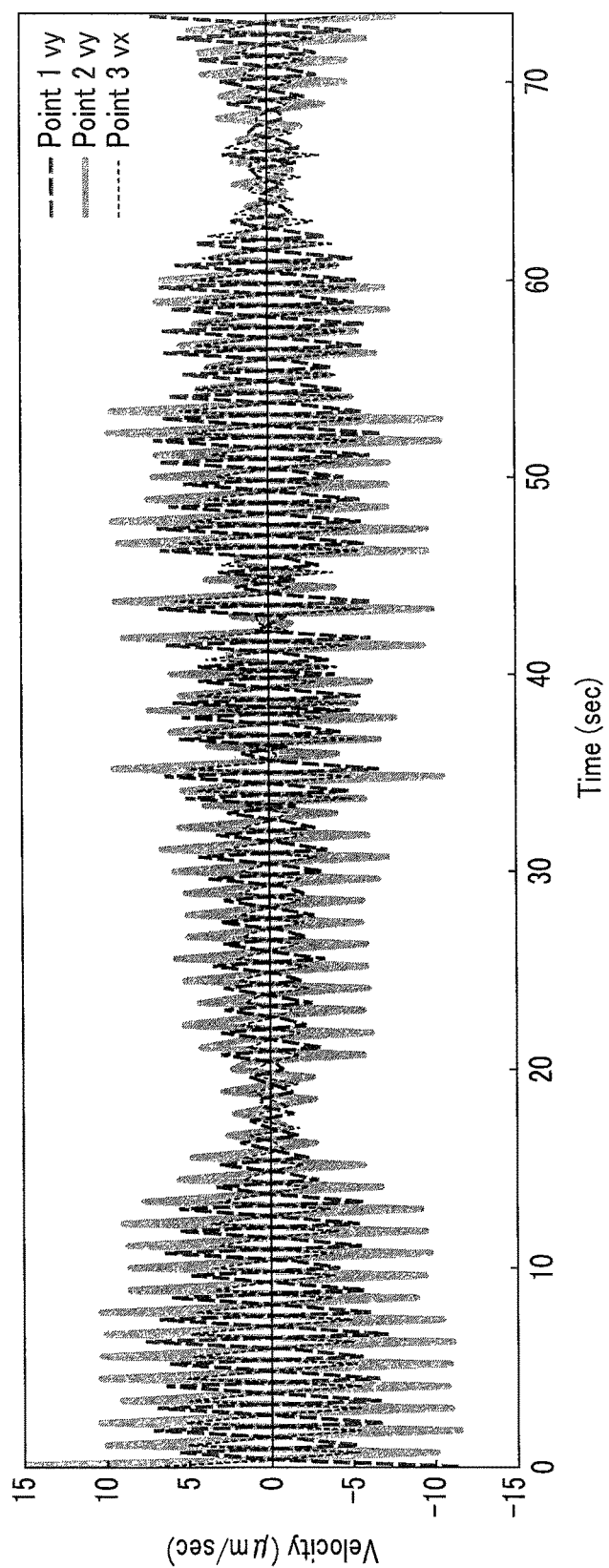
FIG. 18B is a diagram showing how the velocity at each analytic point changes with time after 86 hours from the start of observation.
Figure 18E:
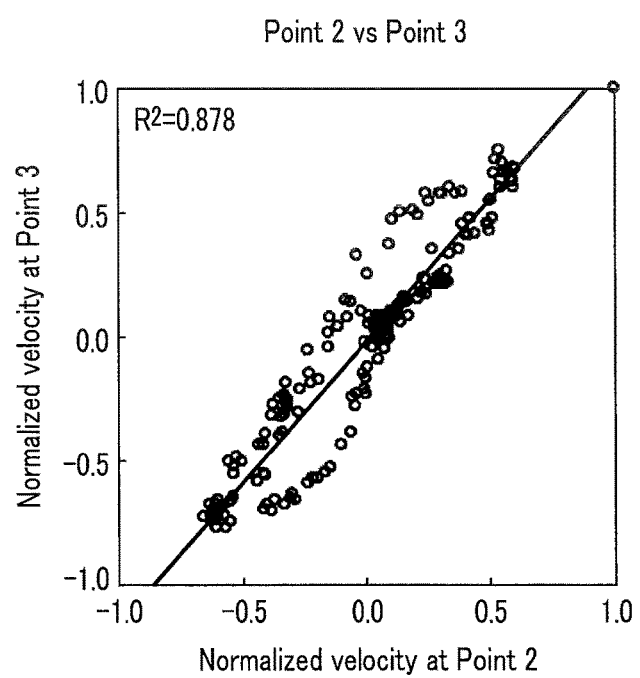
FIG. 18E is a diagram showing how the velocity relation between the second point P2 and the third point P3 is after 86 hours from the start of observation.

Similarly, regarding data obtained 86 hours after the start of observation shown in FIG. 18B, FIG. 18C shows a diagram in which the velocity at the first point P1 is plotted as the horizontal axis component and the velocity at the second point P2 is plotted as the vertical axis component, FIG. 18D shows a diagram in which the velocity at the first point P1 is plotted as the horizontal axis component and the velocity at third point P3 is plotted as the vertical axis component, and FIG. 18E shows a diagram in which the velocity at the second point P2 is plotted as the horizontal axis component and the velocity at third point P3 is plotted as the vertical axis component.

Figure 19A:
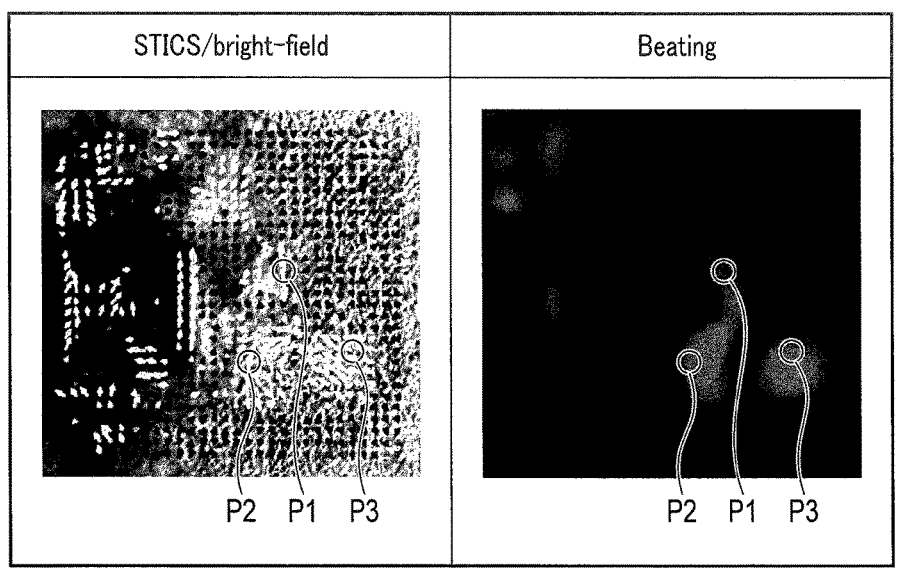
FIG. 19A is a diagram showing an image in which an analytic result obtained by the image correlation method is superimposed on a bright-field image of cells, and an image showing beating strength after 91 hours from the start of observation.
Figure 19B:
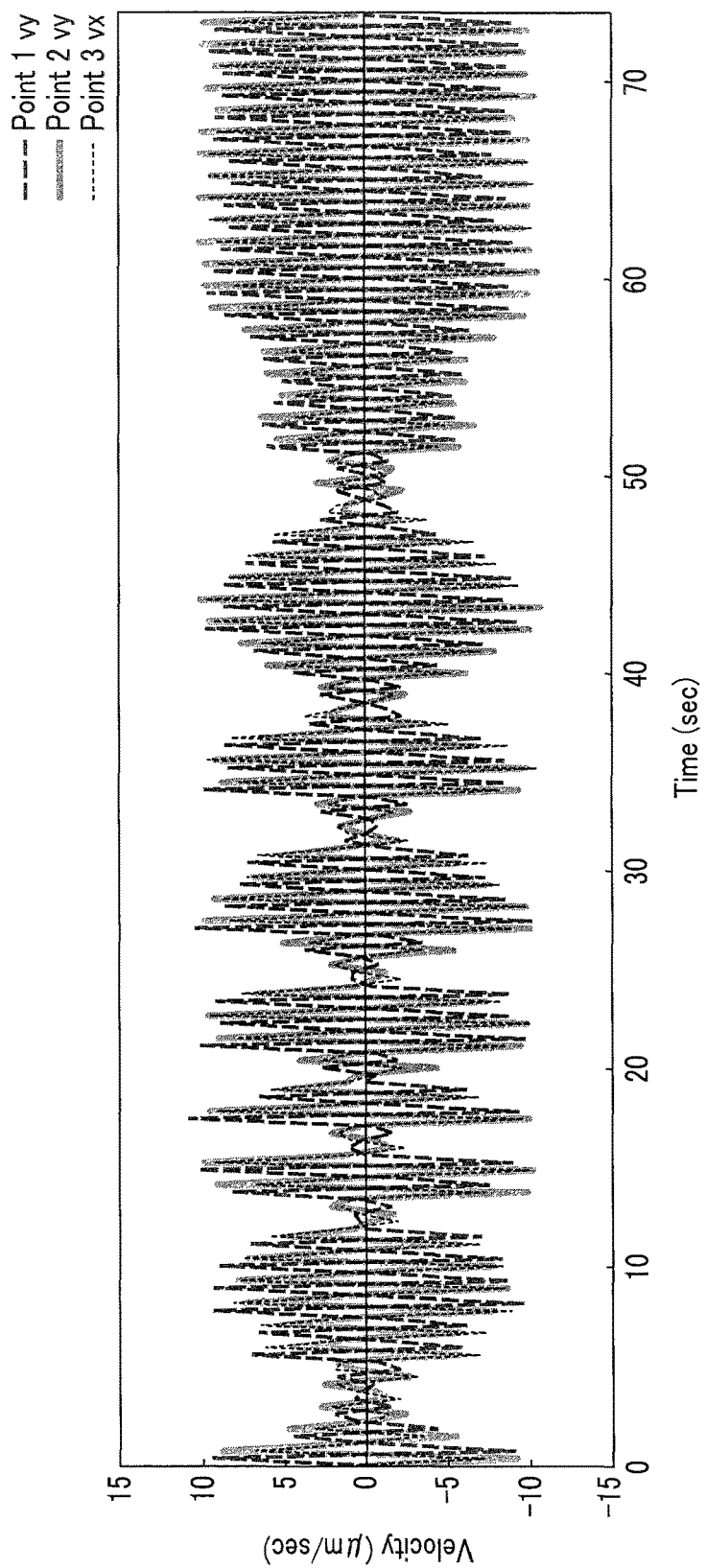
FIG. 19B is a diagram showing how the velocity at each analytic point changes with time after 91 hours from the start of observation.
Figure 19E:
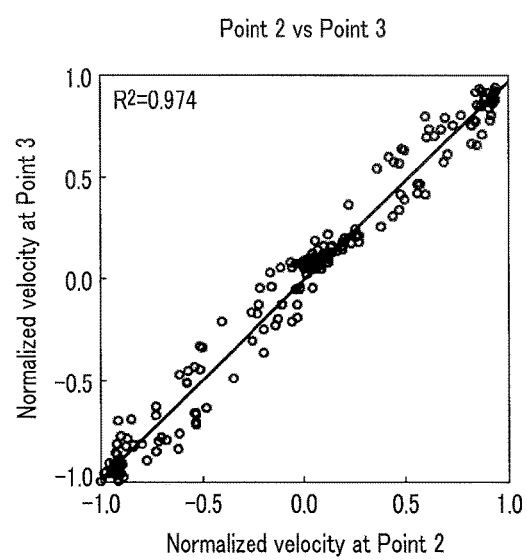
FIG. 19E is a diagram showing how the velocity relation between the second point P2 and the third point P3 is after 91 hours from the start of observation.

Similarly, regarding data 91 hours obtained after the start of observation shown in FIG. 19B, FIG. 19C shows a diagram in which the velocity at the first point P1 is plotted as the horizontal axis component and the velocity at the second point P2 is plotted as the vertical axis component, FIG. 19D shows a diagram in which the velocity at the first point P1 is plotted as the horizontal axis component and the velocity at third point P3 is plotted as the vertical axis component, and FIG. 19E shows a diagram in which the velocity at the second point P2 is plotted as the horizontal axis component and the velocity at third point P3 is plotted as the vertical axis component.

As shown in these drawings, the coefficient of determination $R^2$ increased at all the positions of the first point P1, the second point P2, and the third point P3 with elapsed time from the start of observation. That is, it was elucidated that beating observed at each position with elapsed time from the start of observation showed higher synchronization.

Figure 16F:
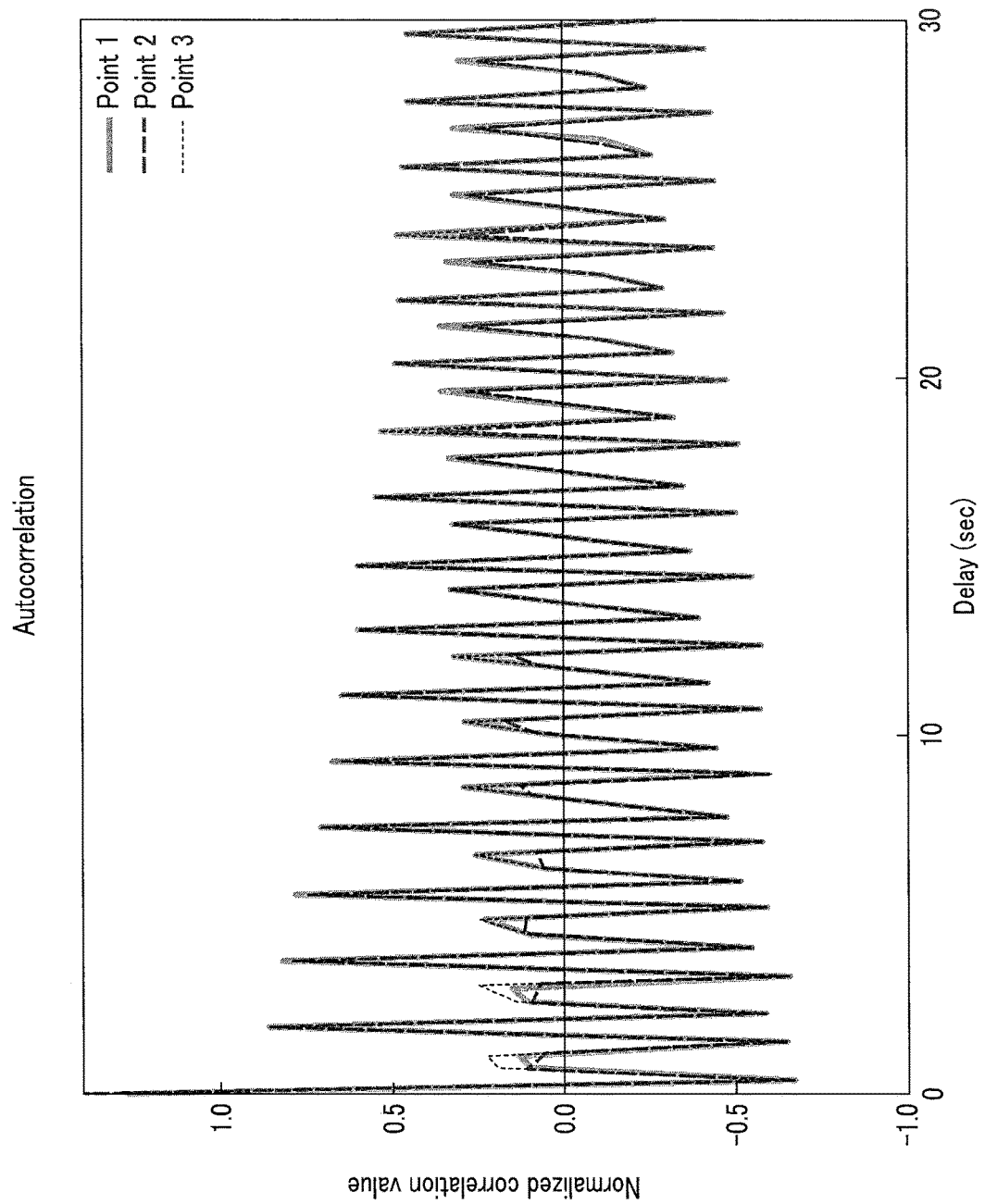
FIG. 16F is a diagram showing how an autocorrelation of velocity is after 76 hours from the start of observation.

Regarding the data obtained 76 hours after the start of observation shown in FIG. 16B, the results of autocorrelations are shown in FIG. 16F. In FIG. 16F, a solid line indicates an autocorrelation regarding the velocity at the first point P1 (Point 1), a broken line indicates an autocorrelation regarding the velocity at the second point P2 (Point 2), and a dotted line indicates an autocorrelation regarding the velocity at the third point P3 (Point 3). Here, values are normalized so that the maximum value is 1.

Figure 16G:
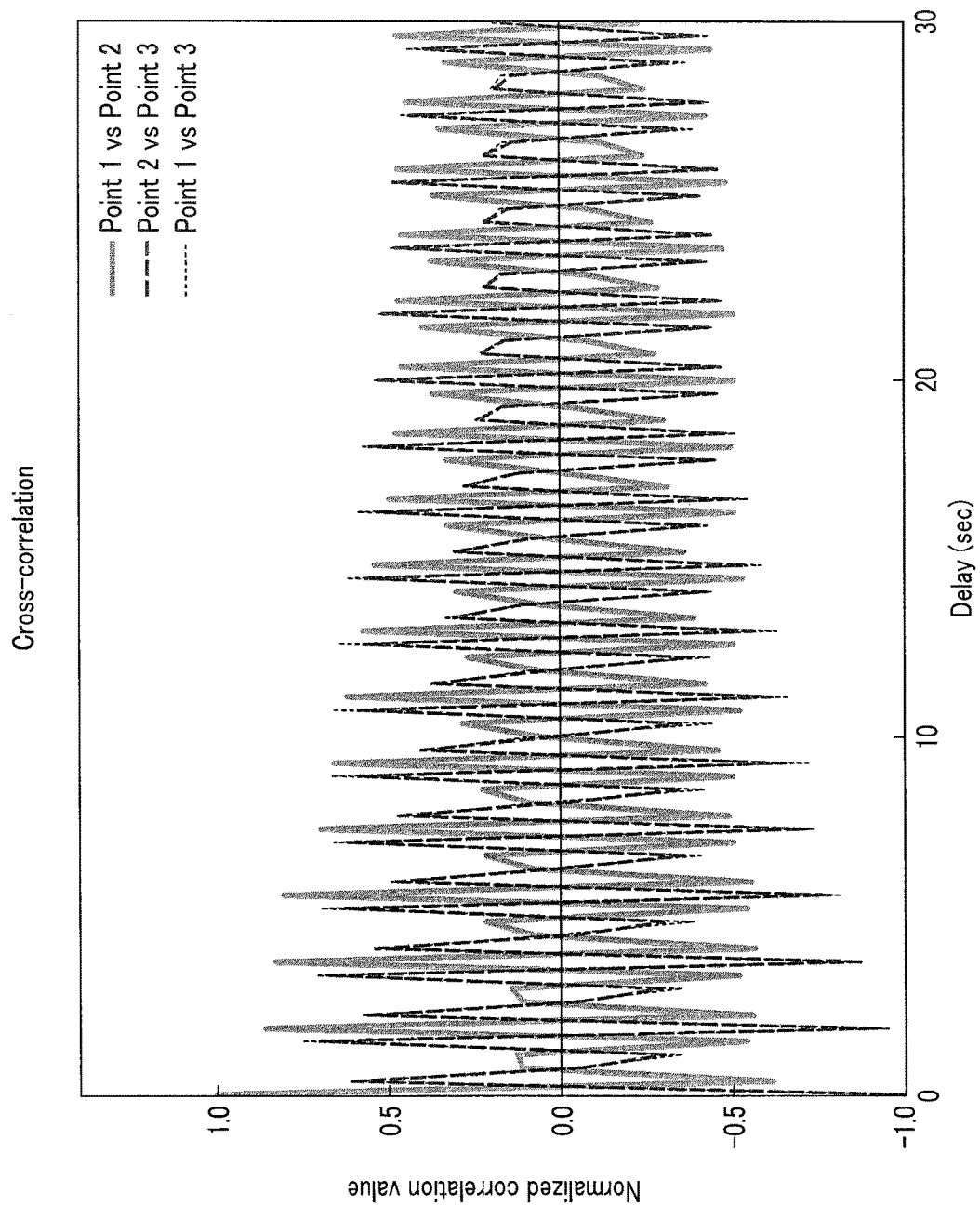
FIG. 16G is a diagram showing how a cross-correlation of velocity is after 76 hours from the start of observation.

Regarding the data obtained 76 hours after the start of observation shown in FIG. 16B, the results of cross-correlations are shown in FIG. 16G. In FIG. 16G, a solid line indicates a cross-correlation between the velocity at the first point P1 and the velocity at the second point P2, a broken line indicates a cross-correlation between the velocity at the second point P2 and the velocity at the third point P3, and a dotted line indicates a cross-correlation between the velocity at the first point P1 and the velocity at the third point P3. In this drawing, values are normalized as well so that the maximum value is 1.

Figure 17G:
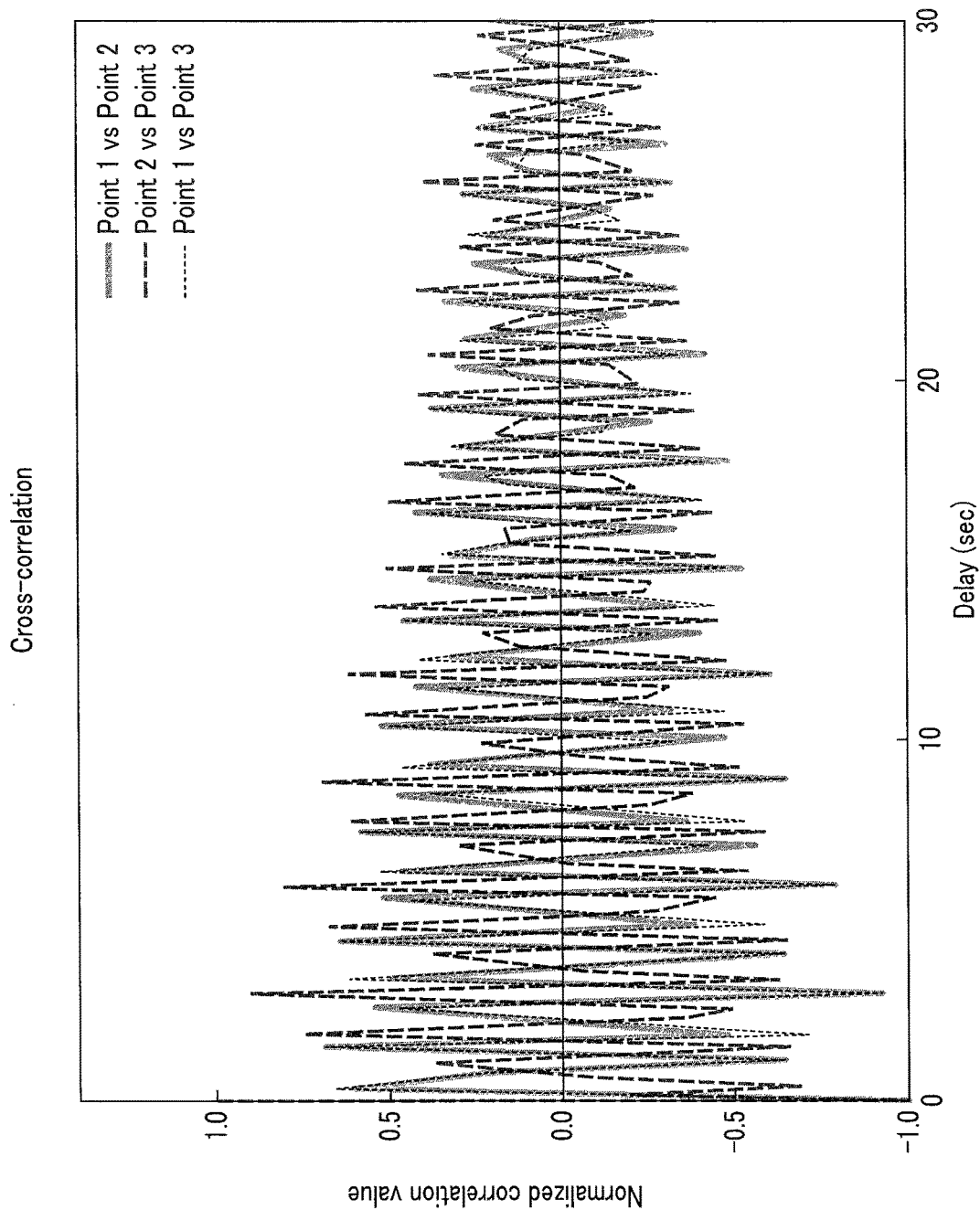
FIG. 17G is a diagram showing how a cross-correlation of velocity is after 81 hours from the start of observation.
Figure 18F:
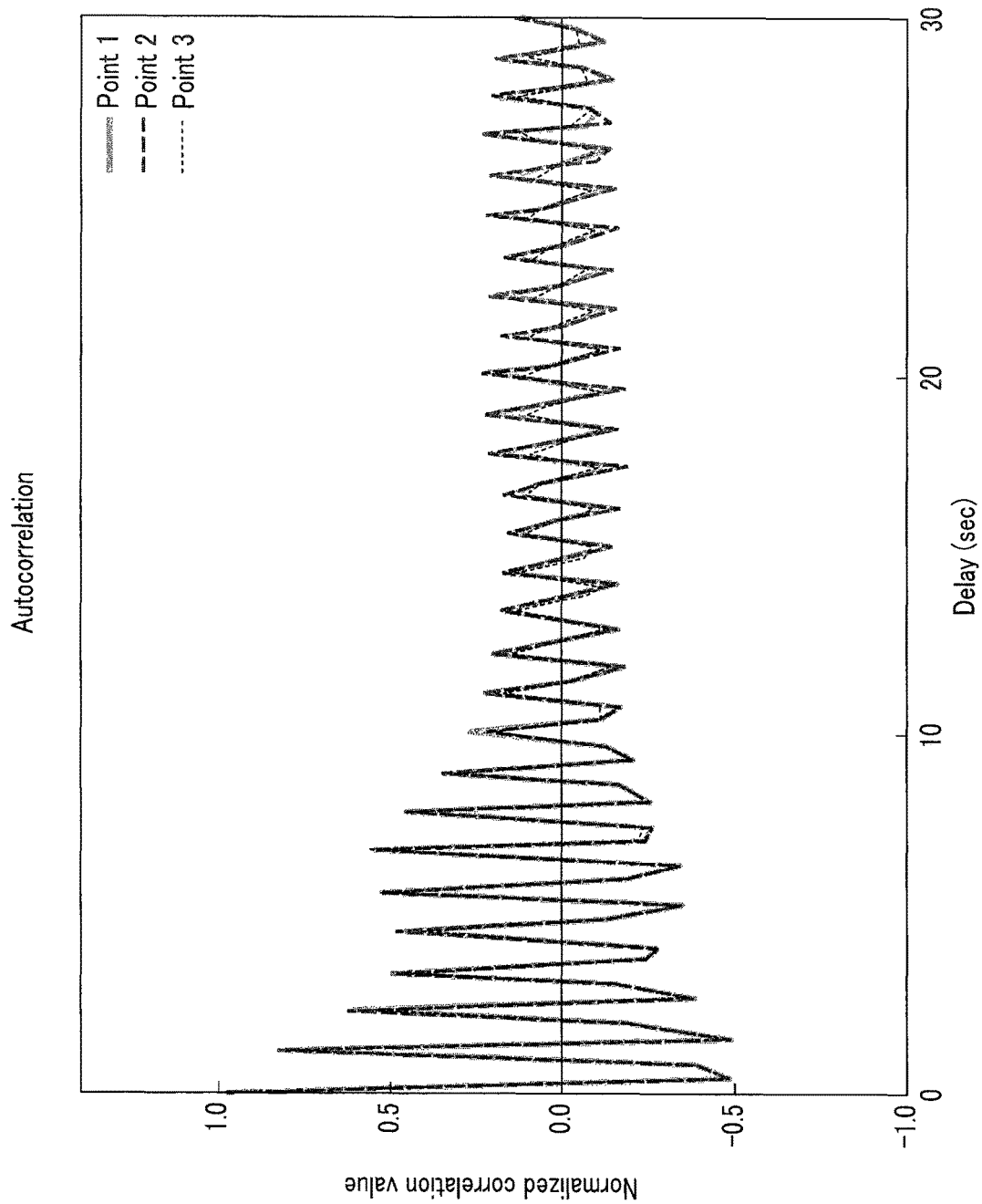
FIG. 18F is a diagram showing how an autocorrelation of velocity is after 86 hours from the start of observation.

Similarly, regarding the data obtained 81 hours after the start of observation shown in FIG. 17B, the results of autocorrelations are shown in FIG. 17F, and the results of cross-correlations are shown in FIG. 17G. Similarly, regarding the data obtained 86 hours after the start of observation shown in FIG. 18B, the results of autocorrelations are shown in FIG. 18F, and the results of cross-correlations are shown in FIG. 18G. Similarly, regarding the data obtained 91 hours after the start of observation shown in FIG. 19B, the results of autocorrelations are shown in FIG. 19F, and the results of cross-correlations are shown in FIG. 19G.

For example, according to FIG. 19F and FIG. 19G showing the analytic results obtained 91 hours after the start of observation in which tendencies are most significantly recognized, it is elucidated that the first point P1, the second point P2, and the third point P3 are always synchronized without any periodic shift. It is also elucidated that beating strength increases and decreases with period of about 7 seconds. It is thus obvious that periodicity and durability can be assessed by the analysis of autocorrelations and cross-correlations.

The relation of the coefficient of determinations shown in FIG. 16C to FIG. 16E, FIG. 17C to FIG. 17E, FIG. 18C to FIG. 18E, and FIG. 19C to FIG. 19E, to the elapsed time after the start of observation is shown in FIG. 20. As shown in FIG. 20, it is clear that the coefficient of determination increases with the elapsed time after the start of observation. That is, it is elucidated that the synchronism of beating increases with elapsed time.

It is also elucidated that the correlation between the second point P2 and the third point P3 is lower than the correlation between first point P1 and the second point P2 and the correlation between the first point P1 and the third point P3. From this, it is presumed that in this example, some information transmission was performed between the cells at the first point P1 and the cells at the second point P2 and between the cells at the first point P1 and the cells at the third point P3. Cells having a pacemaker function can be identified by examining the correlation at each point.

The relation between the elapsed time after the start of observation, beating (right vertical axis), and gene expression (left vertical axis) at the first point P1, the second point P2, and the third point P3 is shown in FIG. 21. Here, the beating represented by a thick line with markers in FIG. 21 corresponds to the standard deviation of velocity shown as "beating" in the images in the fourth column of FIG. 15. The gene expression represented by a thin line is represented by luminescent intensity in the luminescence image. In both the beating and the gene expression, solid lines indicate the results for the first point P1, broken lines indicate the results for the second point P2, and dotted lines indicate the results for the third point P3. In FIG. 21, a straight line parallel to the horizontal axis indicates the maximum values of the beating and the gene expression, and a broken line parallel to the horizontal axis indicates a value half the maximum value (half value) indicated by the solid line. In FIG. 21, the difference between the time at which the gene expression level has reached the half value and the time at which the beating strength has reached the half value is indicated by an arrow and a numerical value.

As shown in FIG. 21, it is elucidated that the times of the gene expression and the functional expression do not coincide with each other. It is elucidated that functions are expressed later than genes particularly at the first point P1 and the second point P2. At the third point P3, the functional expression is earlier than the gene expression.

In the present examples, the expression level of the genes of living cells was analyzed on the basis of the luminescence image, and the beating phenomenon of the same cells in the same period was acquired by the image correlation method based on bright-field sequential images of the same cells acquired in the same period. The luminescence image and the bright-field images could be acquired in the same period in the same cells, and it was therefore shown that the relationship between the gene expression and the functional expression could be assessed as in the present examples. According to the present examples, information such as directionality, strength, and periodicity related to the gene expression and the beating can be provided as visually recognizable information.

A method of analyzing the function of cardiac muscle is, for example, measuring cellular electrical potential by use of multielectrode arrays. However, such a potential measuring method goes no further than a local measurement at positions where electrodes are provided, and does not enable acquisition of information regarding the beating part of the cell group. In contrast, according to the method of analysis using the bright-field image as in the present examples, information such as the positions of cells and the velocity of beating regarding all the cells in an observation field of view can be acquired.

Although velocities are calculated with exposure intervals of 0.61 seconds or 0.37 seconds in the analysis of beating described herein, velocity can be calculated and analyzed using movies taken at exposure intervals different from the exposure intervals in this example, for example, movies taken every one thirtieth of a second.

Example 2-5: Analysis of Elapsed Time of cTnT Expression in Myocardial Differentiation Process of Mouse ES Cells As in Example 2-3, it is possible to observe the process of the myocardial differentiation of the cTnT-GL4 expression mouse ES cells produced in Example 2-1 with time for a long time, and analyze the change of the expression of cTnT.

Example 3: Analysis of Change with Time of Cardiac Muscle-Specific Marker Gene Expression Other than cTnT in Myocardial Differentiation Process of Mouse ES Cells or Mouse iPS Cells The myocardial differentiation process of mouse ES cells or mouse iPS cells can be analyzed with time as in Example 2 even by use of a cardiac muscle-specific marker other than cTnT such as GATA4 or NCX1. For example, the myocardial differentiation process of mouse ES cells or mouse iPS cells can be analyzed even by use of more than one of the aforementioned cardiac muscle-specific markers.

Example 4: Analysis of Change with Time of Cardiac Muscle-Specific Marker Genes by Myocardial Differentiation Enhancing Factor In Example 2 and Example 3 described above, the myocardial differentiation process of mouse ES cells or mouse iPS cells to which a myocardial differentiation enhancing factor is added can be analyzed with time.

Example 5: Analysis of Expression of More than One Gene in Myocardial Differentiation Process Using Undifferentiated Marker/Myocardial Differentiation Marker as Indices The expression of more than one gene can be analyzed by the combination of the myocardial differentiation marker in Example 2 and Example 3 described above and an undifferentiated marker such as Nanog and Tcf3.

Example 6: Analysis of Cardiac Muscle-Specific Marker Expression in Cell Sheet Myocardial Differentiation Process Even if the cell sheet is targeted for analysis, the analyses in Example 2 to Example 5 described above can be conducted.

Example 7: Imaging that Uses Both Luminescence of Cardiac Muscle Marker Expression and Fluorescence in Myocardial Differentiation Process of ES Cells and iPS Cells Fluorescence imaging may be used together in the analysis of the myocardial differentiation described above.

Example 8: Ca Imaging in Myocardial Differentiation Process of ES Cells and iPS Cells Calcium in cells which have differentiated into cardiac muscle cells and started beating can be imaged by use of calcium-responsive luciferase.

(1) Production of Mouse ES Cells and iPS Cells into which Calcium-Responsive Luciferase has been Introduced Mouse ES cells and iPS cells into which calcium-responsive luciferase has been introduced are cultured by use of KO DMEM culture medium on MEF cells whose division has been arrested by a mitomycin C treatment.

A Nucleofection method by Amaxa Nucleofector (Wako Pure Chemical Industries) is used to transfect a vector incorporating calcium-responsive luciferase into the mouse ES cells or iPS cells. The transfected cells are cultured overnight in the KO DMEM culture medium together with neomycin-resistant feeder cells, and the culture medium is replaced with KO DMEM culture medium to which the antibiotic G418 (Invitrogen) is added to a final concentration of 250 µg/ml, whereby a selective culture was conducted. In this way, a stably expressing cell line is acquired. These cells will hereinafter be referred to as calcium-responsive ES cells or calcium-responsive iPS cells.

(2) Formation of Embryoid Body of Calcium-Responsive ES Cells and Calcium-Responsive iPS Cells The cultured calcium-responsive ES cells or calcium-responsive iPS cells are washed with PBS, detached by 0.25% Trypsin-EDTA, and then incubated for 4 hours in an incubator at 37° C. after the KO DMEM culture medium is added thereto. Feeder cells (MEF) are adhered so that the mouse iPS cells alone floated. The culture medium including the cells is centrifuged to collect the cells, and the cells are resuspended in 1 ml of KO DMEM culture medium or IMDM culture medium. The number of cells in the solution is measured by a cell counter, and a cell suspension is added so that the number of cells is 2500 or 5000 in each well with Lipidure-Coat culture medium (96 Well Round Bottom; NOF Cooperation) to which the IMDM culture medium is added. The cells are cultured at 37° C. for 3 to 7 days to form an embryoid body.

(3) Myocardial Differentiation Induction of Calcium-Responsive ES Cells or Calcium-Responsive iPS Cells The formed embryoid body is moved to a gelatin-coated 35 mm dish, and incubated overnight at 37° C. so that the embryoid body adheres to the dish surface. The embryoid body is then cultured at 37° C. for 5 to 14 days to induce its differentiation into beating cardiac muscle cells.

(4) Observation and Analysis of Calcium-Responsive ES Cells or Calcium-Responsive iPS Cells Coelenterazine (manufactured by Wako Pure Chemical Industries) is added to a final concentration of 1 mM to the embryoid body of the calcium-responsive ES cells or the calcium-responsive iPS cells which has been cultured at 37° C. and has come to partly show beating cardiac muscle. The beating cells are observed by use of the bioluminescence microscope LV200 (manufactured by Olympus Corporation) equipped with AQUACOSMOS (Hamamatsu Photonics Corporation). The exposure conditions are as follows. The CCD camera ImagEM (manufactured by Hamamatsu Photonics Corporation) is used under a condition of binning 1×1. The exposure time is set to 15 minutes, and calcium imaging is performed regarding the calcium-responsive ES cells or the calcium-responsive iPS cells.

Example 9: Measurement of Beating Potential in Cell Sheet Derived from ES Cells or iPS Cells Beating potential in a cell sheet derived from ES cells or iPS cells can be measured.

It is possible to measure the beating potential of cells by culturing the cells on, for example, multielectrode arrays.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method for monitoring differentiation into cardiac muscle cells comprising:
introducing, into cells, a reporter gene of luminescent protein configured to vary in luminescence intensity according to an expression of a myocardial differentiation marker gene, wherein the reporter gene is a cTnT gene expression specific luminescent vector, wherein the cells are stem cells or cardiac progenitor cells;
keeping, in an alive state, the cells into which the reporter gene of luminescent protein were introduced;
acquiring a luminescence image as a still image by imaging light emitted from the cells in a light shielding state;
acquiring sequential images with illuminating the cells, the step of acquiring the sequential images comprising acquiring a bright-field image of the cells;
associating biological information obtained from the sequential images with biological information obtained from the still image;
conducting a motion analysis based on the bright-field image, wherein the motion analysis is conducted by use of an image correlation method;
analyzing beating of the cells by the motion analysis;
analyzing expression of the myocardial differentiation marker gene based on the luminescence image; and
assessing a relationship between the beating and the expression.

2. A method for monitoring differentiation into cardiac muscle cells comprising:
introducing, into cells, a reporter gene of luminescent protein configured to vary in luminescence intensity according to an expression of a myocardial differentiation marker gene, wherein the reporter gene is a cTnT gene expression specific luminescent vector, wherein the cells are stem cells or cardiac progenitor cells;
keeping, in an alive state, the cells into which the reporter gene of luminescent protein were introduced;
acquiring a luminescence image as a still image by imaging light emitted from the cells in a light shielding state;
acquiring sequential images with illuminating the cells, the step of acquiring the sequential images comprising acquiring a bright-field image of the cells;
associating biological information obtained from the sequential images with biological information obtained from the still image;
conducting a motion analysis based on the bright-field image,
wherein the motion analysis is conducted by use of an image correlation method.

3. The method according to claim 1, wherein
acquiring the luminescence image comprises acquiring more than one luminescence image by imaging with time, and
the method further comprises acquiring a change in luminescence intensity based on the luminescence images so that a state of differentiation of the cells is identifiable.

4. The method according to claim 3, further comprising converting the change in luminescence intensity into a numerical value.

5. The method according to claim 1, further comprising introducing reporter gene of a luminescent protein configured to emit light according to an expression of an undifferentiated marker gene.

6. The method according to claim 1, wherein the reporter gene is configured to emit light according to the expression of the myocardial differentiation marker genes of more than one kind.

7. The method according to claim 1, further comprising determining a state of differentiation of the cells.

8. The method according to claim 1, further comprising analyzing a calcium concentration in the cells.

9. The method according to claim 1, further comprising measuring potential of the cells.

* * * * *

SEQUENCE LISTING

<160> NUMBER OF SEQ ID NOS: 2

<210> SEQ ID NO 1
<211> LENGTH: 37
<212> TYPE: DNA
<213> ORGANISM: Artificial Sequence
<220> FEATURE:
<223> OTHER INFORMATION: Forward primer 1

-continued

```
<400> SEQUENCE: 1
gcctcgagtc tagactgaga tacaatgcaa aagctgg                              37

<210> SEQ ID NO 2
<211> LENGTH: 34
<212> TYPE: DNA
<213> ORGANISM: Artificial Sequence
<220> FEATURE:
<223> OTHER INFORMATION: Reverse primer 1

<400> SEQUENCE: 2
gcagatctgg ttgagggcag ggcatgggga gagc                                 34
```